United States Patent
Skufca et al.

(10) Patent No.: US 10,905,831 B2
(45) Date of Patent: Feb. 2, 2021

(54) DELIVERY SYSTEM FOR DELIVERING MEDICAL AND PHARMACEUTICAL COMPOUNDS

(71) Applicant: Peter Skufca, Tuebingen (DE)

(72) Inventors: Peter Skufca, Tuebingen (DE); Peter Maks Skufca, Domzale (SI)

(*) Notice: Subject to any disclaimer, the term of this patent is extended or adjusted under 35 U.S.C. 154(b) by 414 days.

(21) Appl. No.: 15/240,194

(22) Filed: Aug. 18, 2016

(65) Prior Publication Data

US 2016/0354546 A1 Dec. 8, 2016

Related U.S. Application Data

(63) Continuation-in-part of application No. PCT/EP2014/053145, filed on Feb. 18, 2014.

(51) Int. Cl.
*A61M 5/28* (2006.01)
*A61M 5/315* (2006.01)
*A61M 5/31* (2006.01)

(52) U.S. Cl.
CPC ............ *A61M 5/288* (2013.01); *A61M 5/283* (2013.01); *A61M 5/31591* (2013.01); *A61M 2005/3139* (2013.01)

(58) Field of Classification Search
CPC .. A61M 5/2429; A61M 5/178; A61M 5/2033; A61M 5/326; A61M 5/283;
(Continued)

(56) References Cited

U.S. PATENT DOCUMENTS 2,478,844 A * 8/1949 Smith .................. A61M 5/283
604/203
3,413,975 A 12/1968 Hein ............................ 128/253
(Continued)

FOREIGN PATENT DOCUMENTS

DE 1207043 B 4/1962
DE 3924830 A1 7/1989
(Continued)

OTHER PUBLICATIONS

Office action dated Jan. 19, 2018 from the Russian Patent Office in the related foreign application RU2016137123 and English translation of the Jan. 19, 2018 Office action (4 pages).
International Search Report of European Patent Office dated Nov. 5, 2014 in related International Application PCT/EP2014/053145 (10 pages).
(Continued)

*Primary Examiner* — Scott J Medway
(74) *Attorney, Agent, or Firm* — Imperium Patent Works; Darien K. Wallace

(57) ABSTRACT

A delivery system for medical and pharmaceutical compounds includes a container, a closure element, a supporting element and a penetration element. The container contains the compounds and has a closed container bottom and an open second end. The closure element makes fluid-tight contact with the inner wall of the container. The supporting element attaches to the closure element. The penetration element has a hollow needle and moves along the longitudinal axis of the container. The penetration element includes a first link motion portion, and the supporting element includes a second link motion portion. The first link motion portion has a guiding groove, and the second link motion portion has a projection. The hollow needle of the penetration element moves towards the container bottom and penetrates the closure element. The penetration element moves inside the supporting element towards the container bottom based on how the projection travels in the guiding groove.

22 Claims, 9 Drawing Sheets

(58) Field of Classification Search
CPC ........ A61M 2005/2013; A61M 5/3234; A61M 5/24; A61M 2005/3114
See application file for complete search history.

(56) References Cited

U.S. PATENT DOCUMENTS

| | | | | |
|---|---|---|---|---|
| 3,736,932 | A * | 6/1973 | Satchell | A61M 5/178 604/190 |
| 3,931,815 | A * | 1/1976 | Takatsuki | A61B 5/150732 600/577 |
| 4,425,120 | A * | 1/1984 | Sampson | A61M 5/3271 604/198 |
| 4,445,895 | A * | 5/1984 | Margulies | A61M 5/24 604/193 |
| 4,568,336 | A | 2/1986 | Cooper | 604/240 |
| 4,813,940 | A * | 3/1989 | Parry | A61M 5/283 604/198 |
| 4,900,311 | A * | 2/1990 | Stern | A61M 5/3271 604/198 |
| 4,917,673 | A * | 4/1990 | Coplin | A61M 5/3271 604/198 |
| 4,927,414 | A * | 5/1990 | Kulli | A61M 5/3234 604/110 |
| 5,015,229 | A * | 5/1991 | Meyer | A61F 9/0017 604/184 |
| 5,232,456 | A * | 8/1993 | Gonzalez | A61M 5/3234 604/192 |
| 5,242,401 | A * | 9/1993 | Colsky | A61M 5/326 604/110 |
| 5,403,288 | A * | 4/1995 | Stanners | A61M 5/322 604/110 |
| 5,423,758 | A | 6/1995 | Shaw | 604/110 |
| 5,688,241 | A * | 11/1997 | Asbaghi | A61M 5/326 604/110 |
| 5,695,475 | A * | 12/1997 | Best, Jr. | A61M 5/3243 128/919 |
| 5,984,899 | A * | 11/1999 | D'Alessio | A61M 5/3271 604/192 |
| 6,039,713 | A | 3/2000 | Botich et al. | 604/110 |
| 6,123,688 | A * | 9/2000 | Botich | A61M 5/24 604/110 |
| 6,547,764 | B2 * | 4/2003 | Larsen | A61M 5/326 604/110 |
| 7,214,221 | B2 * | 5/2007 | Fentress | A61M 5/145 604/890.1 |
| 7,344,517 | B2 * | 3/2008 | Schiller | A61M 5/3234 604/110 |
| 7,470,258 | B2 * | 12/2008 | Barker | A61M 5/3234 604/192 |
| 8,128,594 | B1 * | 3/2012 | Chang | A61M 5/3272 604/110 |
| 9,907,916 | B2 * | 3/2018 | Evans | A61M 5/3272 |
| 10,524,833 | B2 * | 1/2020 | Katkar | A61B 90/06 |
| 2006/0189933 | A1 * | 8/2006 | Alheidt | A61M 5/326 604/110 |
| 2007/0078408 | A1 * | 4/2007 | Wang | A61M 5/24 604/198 |
| 2007/0293826 | A1 * | 12/2007 | Wall | A61M 5/19 604/200 |
| 2009/0005742 | A1 * | 1/2009 | Liversidge | A61M 5/326 604/263 |
| 2009/0227956 | A1 * | 9/2009 | Emmott | A61M 5/002 604/196 |
| 2011/0213304 | A1 * | 9/2011 | Schraga | A61M 5/3234 604/110 |
| 2011/0319832 | A1 * | 12/2011 | Chun | A61M 5/326 604/198 |
| 2011/0319833 | A1 * | 12/2011 | Chun | A61M 5/326 604/198 |
| 2013/0018323 | A1 * | 1/2013 | Boyd | A61M 5/2448 604/191 |
| 2014/0052071 | A1 * | 2/2014 | Pickhard | A61M 5/288 604/192 |
| 2014/0102048 | A1 | 4/2014 | Arnitz et al. | 53/467 |
| 2015/0190586 | A1 * | 7/2015 | Takemoto | A61M 5/3213 604/198 |
| 2016/0008779 | A1 * | 1/2016 | Seaward | B01F 11/0054 366/273 |
| 2016/0263320 | A1 * | 9/2016 | Constantineau | A61M 5/19 |
| 2018/0126091 | A1 * | 5/2018 | Fraas | A61M 5/326 |

FOREIGN PATENT DOCUMENTS

| | | |
|---|---|---|
| DE | 19652708 A1 | 12/1996 |
| DE | 10121232 C2 | 4/2001 |
| DE | 10340613 A1 | 8/2003 |
| EP | 0298585 | 5/1988 |
| EP | 0312035 A2 | 10/1988 |
| EP | 0707859 A1 | 6/1995 |
| EP | 2535073 A1 | 6/2011 |
| RU | 99101749 A | 1/1999 |

OTHER PUBLICATIONS

International Organization for Standardization ISO 8362-1 standard for injection containers and accessories Part 1, third edition Dec/ 15, 2009 [ISO 8362-1:2009 (E)] (10 pages).
International Organization for Standardization ISO 8362-2 standard for injection containers and accessories Part 2, second edition Oct. 15, 2008 [ISO 8362-2:2008 (E)] (10 pages).
International Organization for Standardization ISO 11040-4 standard for prefilled syringes Part 4, second edition Feb. 1, 2007 [ISO 11040-4:2007 (E)] (14 pages).
International Organization for Standardization ISO 11040-5 standard for prefilled syringes Part 5, third edition Jan. 15, 2012 [ISO 11040-5:2012 (E) ] (10 pages).

* cited by examiner

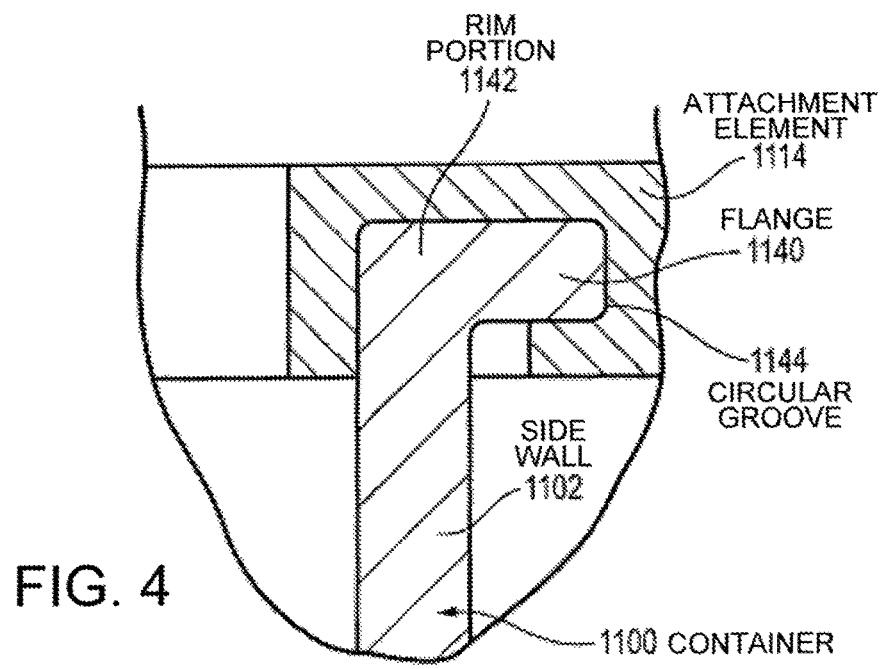
FIG. 4
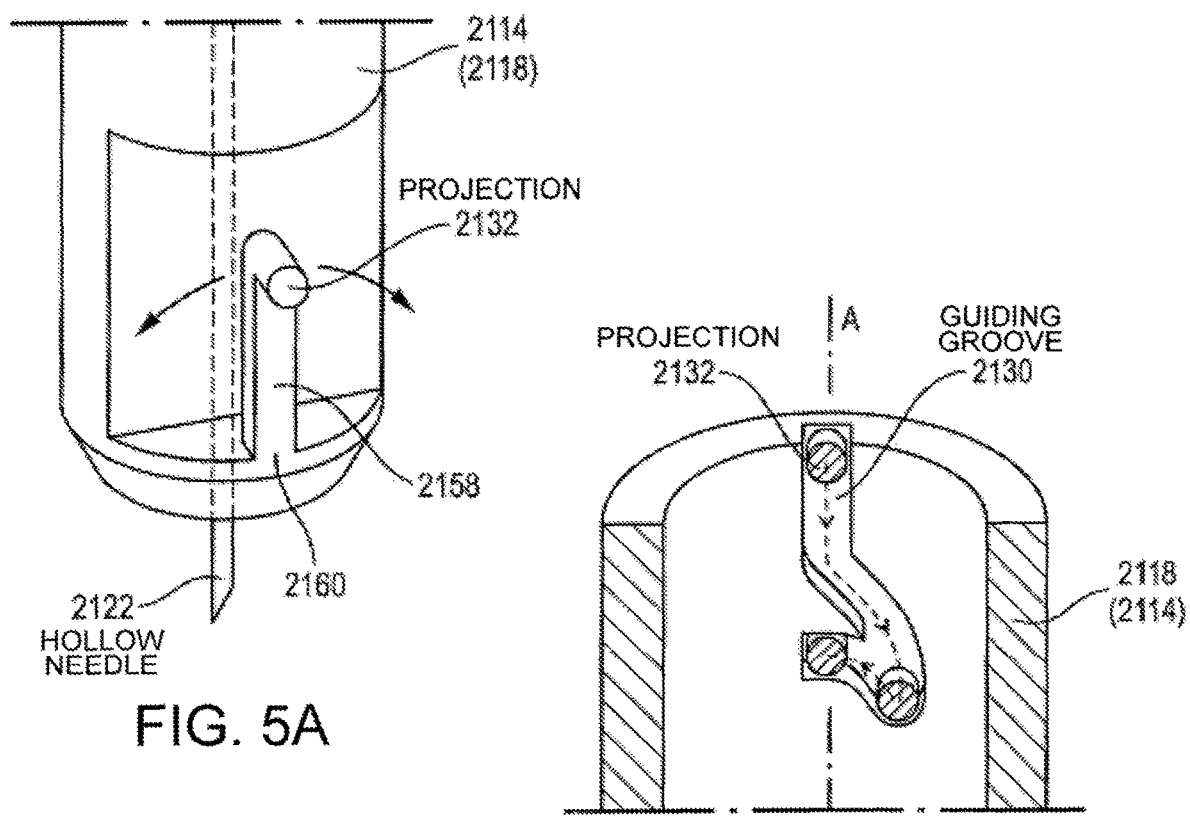
FIG. 5A
FIG. 5B

DELIVERY SYSTEM FOR DELIVERING MEDICAL AND PHARMACEUTICAL COMPOUNDS

CROSS REFERENCE TO RELATED APPLICATION

This application is filed under 35 U.S.C. § 111(a) and is based on and hereby claims priority under 35 U.S.C. § 120 and § 365(c) from International Application No. PCT/EP2014/053145, filed on Feb. 18, 2014, and published as WO 2015/124172 A1 on Aug. 27, 2015. This application is a continuation-in-part of International Application No. PCT/EP2014/053145. International Application No. PCT/EP2014/053145 is pending as of the filing date of this application, and the United States is an elected state in International Application No. PCT/EP2014/053145, which is incorporated herein by reference.

TECHNICAL FIELD

The invention relates to a delivery system for delivering medical and pharmaceutical compounds.

BACKGROUND

A prior art delivery system for delivering medical or pharmaceutical compounds is described in EP2535073 A1 and includes a first container that stores the compounds, a closure element accommodated within the first container, and an extraction unit adapted to extract the compounds automatically once the closure element has been manually penetrated. In this known system, the first container is accommodated within a second container that serves, on the one hand, as a holding means for holding an energy unit used to carry out the above-mentioned automatic function and, on the other hand, as a support means to assist the first container in maintaining the extraction unit in a well-defined positional relationship with respect to the first container. That is, in order to put into effect the above-mentioned automatic delivery function, a container-container arrangement is provided that renders the overall structure complicated and accident-sensitive.

It is an object of the present invention to improve the reliability of the above known system by providing a delivery system for delivering medical and pharmaceutical compounds that dispenses with the above-mentioned automatic function.

SUMMARY

The present invention relates to a delivery system for delivering medical or pharmaceutical compounds that includes (a) a container unit with (a-a) a container for storing the compounds that has a circumferential wall, a first end closed by a container bottom and an open second end, wherein the container unit has a longitudinal axis, and (a-b) a closure element disposed within the container in a fluid-tight contact with the circumferential wall, and (b) an extraction unit that includes a supporting element supported at the closure element and a penetration element having a hollow needle adapted to penetrate the closure element. The penetration element is fitted to the supporting element so as to be movable relative to the supporting element along the longitudinal axis. Furthermore, the penetration element includes a first link motion portion, and the supporting element includes a second link motion portion. One of the first or second link motion portions is provided with a projection, and the other one is provided with a guiding groove. The projection and the guiding groove are engageable with each other to form a link motion adapted to make the penetration element move relative to the supporting element in a predetermined way towards the container bottom, thereby making the hollow needle penetrate the closure element.

In another embodiment, a delivery system for delivering medical and pharmaceutical compounds includes a container, a closure element, a supporting element and a penetration element. The container contains a liquid solution of the compounds and has a first end closed by a container bottom and an open second end. The closure element makes fluid-tight contact with the cylindrical wall of the container. The supporting element is attached to the closure element. The penetration element has a hollow needle and moves relative to the supporting element along the longitudinal axis of the container. A compression spring is disposed between the penetration element and the closure element. The penetration element includes a first link motion portion, and the supporting element includes a second link motion portion. A projection is disposed on one of the first or second link motion portions, and the other of the first or second link motion portions has a guiding groove. The hollow needle of the penetration element moves towards the container bottom and penetrates the closure element. The penetration element moves relative to the supporting element towards the container bottom based on how the projection travels in the guiding groove.

The first link motion portion fits into the second link motion portion, and the penetration element is disposed within and longitudinally guided by the supporting element. The container has a rim portion at the second end, and an attachment element is fitted onto the container over the rim portion. The attachment element surrounds and slides along the supporting element. The delivery system also includes a mounting element that is connected to the supporting element. The mounting element has a finger flange. The mounting element engages the rim portion of the container at the open second end of the container. The mounting element is deformable and snaps over the attachment element to allow the attachment element to slide inside the mounting element.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 4 is a schematic enlarged view of the upper end of an alternative container having a flange portion.

FIG. 5A is a schematic drawing illustrating a first alternative of a link motion of the delivery system according to the present invention.

FIG. 5B is a schematic drawing illustrating a second alternative of the link motion of the delivery system.

DETAILED DESCRIPTION

Reference will now be made in detail to some embodiments of the invention, examples of which are illustrated in the accompanying drawings. In the description and claims, terms such as "upper", "lower", "top", "bottom", "up", "down", "upwards" and "downwards" are used to describe relative directions and orientations between different parts of the system, and it is to be understood that the overall structure being described can actually be oriented in any way in three-dimensional space.

Figure 1A:
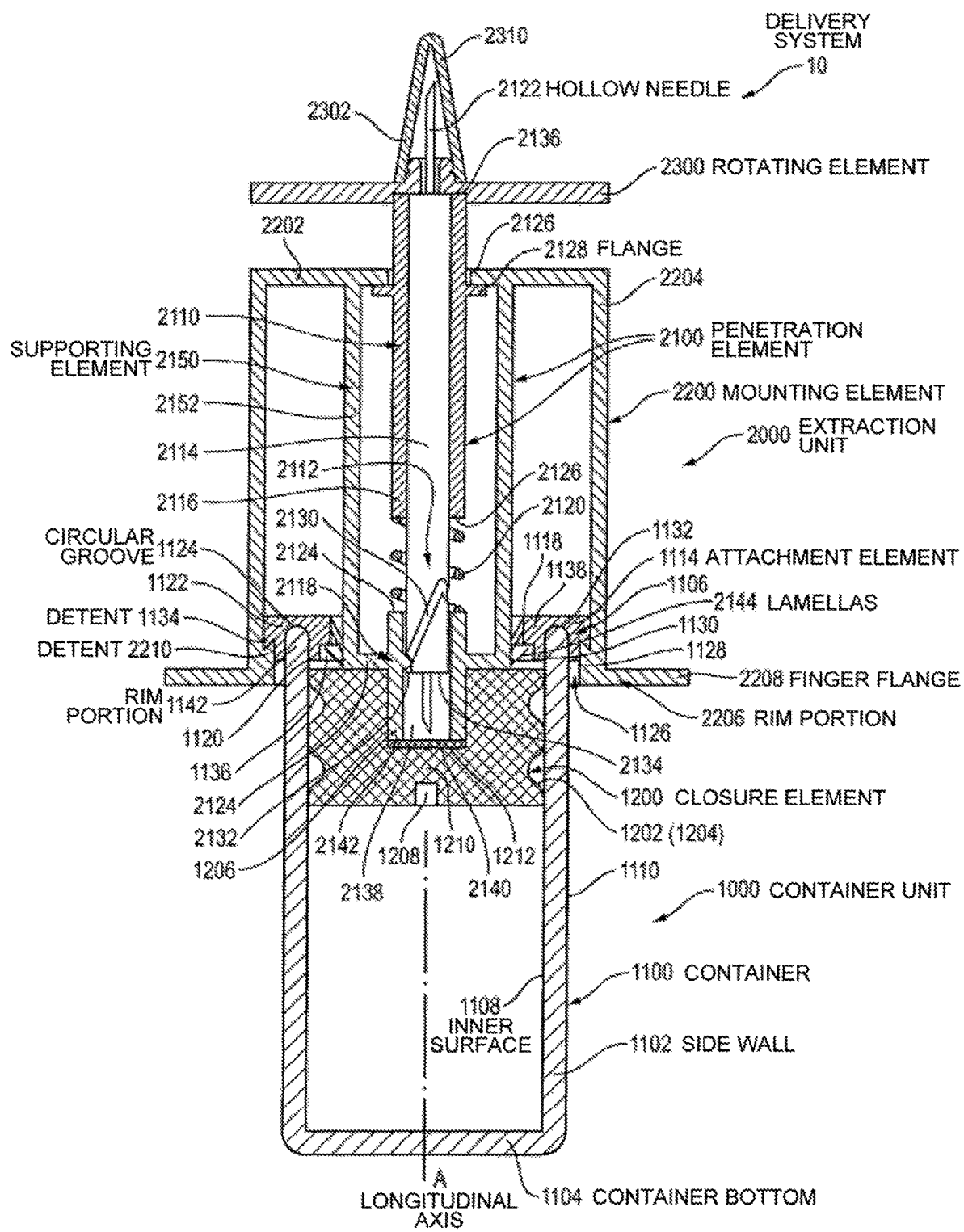
FIG. 1A is a schematic drawing of a delivery system in an initial state according to a preferred embodiment of the present invention.

FIG. 1A shows a delivery system 10 for delivering medical or pharmaceutical compounds. The delivery system includes a container unit 1000 and an extraction unit 2000. The container unit 1000 has a longitudinal axis A and includes a container 1100 and a closure element 1200. The container 1100 is used to store the compounds and has a circumferential wall, a first end closed by a container bottom 1104 and an open second end. The closure element 1200 is accommodated within the container 1100 and is in a fluid-tight contact with the circumferential wall. The extraction unit 2000 includes a supporting element 2150 supported at the closure element 1200 and a penetration element 2100 having a hollow needle 2122 adapted to penetrate the closure element.

The penetration element 2100 is fitted to the supporting element 2150 so as to be movable relative to the supporting element along the longitudinal axis A. The extraction unit 2000 includes a first link motion portion 2112 and a second link motion portion 2118. The first link motion portion 2112 is provided at the penetration element 2100, while the second link motion portion 2118 is provided at the supporting element 2150. One of the first link motion portion 2112 or second link motion portion 2118 is provided with a projection 2132, and the respective other one is provided with a guiding groove 2130. The projection 2132 and the guiding groove 2130 are engageable with each other and form a link motion adapted to make the penetration element 2100 move relative to the supporting element 2150 in a predetermined way towards the container bottom 1104, thereby making the hollow needle 2122 penetrate the closure element 1200. The extraction unit 2000 is, in structural and functional terms, divided into the penetration element 2100 that includes the first link motion portion 2112 and the supporting element 2150 that includes the second link motion portion 2118. Because the supporting element 2150 is supported at the closure element 1200, the penetration element 2100 is movable relative to the closure element.

In terms of the support of the supporting element 2150 at the closure element 1200, the supporting element may be coupled to the closure element in a form locking manner and/or force locking manner. A coupling in a form locking manner and/or force locking manner enables the transfer of a longitudinal force from the penetration element 2100 to the supporting element 2150 and, thus, to the closure element 1200. The supporting element 2150 may be stably coupled to the closure element 1200, e.g., by a press-fit or by bonding, or may be releasably coupled to the closure element, e.g., by a press-fit or by screwing.

The terms deliver, extract and discharge each emphasize a specific perspective. Deliver refers to the inventive system in its entirety in the general meaning of dispense or give off or the more specific meaning of administer in case of delivering compounds to an individual. Extract refers to the extraction unit 2000 in order to focus on the process or operation of removing or taking out the compounds from the container 1100 without regard to the purpose of this process and irrespective of what is to be achieved with the compounds. Discharge refers to the transport of the compounds from the container 1100 through the hollow needle 2122 to the outside of the (entire) system, i.e., objectively to the penetration element 2100.

The medical and pharmaceutical compounds are liquids that are in contact with the container 1100 and the closure element 1200. Therefore, the container 1100 together with the closure element 1200 forms a primary packaging for the compounds in conformity with the Guidelines on Packaging for Pharmaceutical Products, issued in the WHO Technical Report Series, No. 902, 2002, which provide that a primary packaging must protect the pharmaceutical or medical products against all adverse external influences that may affect their quality or potency such as, for example, light, moisture, oxygen, biological contamination or mechanical damage. In particular, such a primary packaging must not interact physically or chemically with the contained medical or pharmaceutical compounds in any way that would alter their quality. Specifically, a primary packaging must protect the contents from extraneous matter, from loss of the substance, and from efflorescence, deliquescence and evaporation under normal conditions of handling, shipping or storage.

The container 1100 and the closure element 1200 are parts of the container unit 1000. That is, the container unit 1000 includes at least these elements but may contain more than these elements. The container 1100 essentially has a right-cylindrical shape, i.e., the shape of a mathematical cylinder having its axis (the above-mentioned longitudinal axis A) perpendicular to its base. The container 1100 may be thought of as being made up of a tube or barrel (its circumferential or side wall) of undefined cross-section, having its longitudinal axis perpendicular to each of the virtual planes closing its ends. Each virtual plane may be curved or bulged. One of the container ends is connected to or firmly closed by the container bottom 1104, such that the container bottom is not non-destructively removable. The container bottom 1104 may or may not completely lie within the virtual plane at the end of the container 1100. Preferably, the cross-section of the container 1100 is symmetric with respect to the longitudinal axis A so that the longitudinal axis is an axis of symmetry.

In order to enable handling and processing of the container 1100 in conventional filling facilities and with conventional technology used for filling and processing of standardized syringes, the container 1100 may meet, in terms of shape and dimensions, selected specifications of ISO 11040-4 standard of a prefilled syringe. All cross-sections perpendicular to the longitudinal axis A or axis of symmetry may be circles. Especially in this regard, the container 1100 may include or form a flange portion along its open second end.

The paragraphs below describe the preferred dimensions of the container 1100 according to various standards. Following the terminology used in these standards, the container 1100 without the flange portion is called a barrel.

The cylindrical barrel complies, in terms of its inner diameter, outer diameter and wall thickness, with the relevant specifications of the above-mentioned ISO 11040-4 standard for a suitable specific standardized nominal volume. The specific standardized nominal volume may correspond to or may only slightly differ from, the predetermined filling volume of the container 1100. Thus, the chosen volume of the container 1100 is a suitable one of the various nominal volumes provided by the ISO 11040-4 standard. In particular, the cylindrical barrel may be formed to meet the barrel diameters d1 and d2 and the barrel wall thickness s1 as indicated in FIG. 1 and Table 1 of the ISO 11040-4 standard for a specific standardized nominal volume of a standardized syringe. Depending on the predetermined filling volume, the length of the barrel may conform to the length l1 or total length l of a standardized syringe as indicated in FIG. 1 and Table B.1 of ISO 11040-4 standard, or may vary within a range defined by the length l1 and the total length l as aforementioned, or may even be different from the specifications of the ISO 11040-4 standard.

Generally, the length of the cylindrical barrel is defined and set so that the predetermined filling can be achieved with the inner diameter, outer diameter, and wall thickness adopted from the ISO 11040-4 standard for the specific nominal volume as above explained. If the predetermined filling volume matches a standardized nominal volume of a standardized syringe, the standardized nominal volume may be used as the specific nominal volume and the cylindrical barrel may be formed to meet the barrel diameters d1 and d2 and the barrel wall thickness s1 as indicated in FIG. 1 and Table 1 of the ISO 11040-4 standard for this standardized or specific nominal volume. In this case, the length of the barrel may meet the length l1 indicated in FIG. 1 and Table 1 of the ISO 11040-4 standard for the standardized nominal volume. If the predetermined filling volume differs from any of the nominal volumes set by the ISO 11040-4 standard, any suitable nominal volume close to the predetermined filling volume may be used as the specific nominal volume, and the cylindrical barrel may be formed to meet the barrel diameters d1 and d2 and the barrel wall thickness s1 as indicated in FIG. 1 and Table 1 of the ISO 11040-4 standard for this suitable or specific nominal volume.

Even if the predetermined filling volume matches a standardized nominal volume of a standardized syringe, however, any other suitable standardized nominal volume may be used as the specific nominal volume, and the cylindrical barrel may be formed to meet the barrel diameters d1 and d2 and the barrel wall thickness s1 as indicated in FIG. 1 and Table 1 of the ISO 11040-4 standard for this other standardized or specific nominal volume. For example, if the predetermined filling volume is 1 ml, the cylindrical barrel may meet the outer diameter d1, inner diameter d2, and wall thickness s1 of a 1 ml syringe in a long version, with d1 being 8.15 mm±0.1 mm, d2 being 6.35 mm±0.1 mm, and s1 being approximately 0.9 mm (cf. ISO 11040-4, Tables 1 and B.1 for a nominal volume of 1 ml). In this case, the barrel length may meet the length l1 of the 1 ml syringe in the long version, being 54 mm±0.5 mm, with the specific nominal volume being 1 ml. With the same predetermined filling volume of 1 ml, however, the cylindrical barrel may alternatively meet the outer diameter d1 (=10.85 mm±0.1 mm), inner diameter d2 (=8.65 mm±0.2 mm), and wall thickness s1 (•1.1 mm) of a 1 ml syringe in a short/standard version (cf. ISO 11040-4, Tables 1 and B.1 for a nominal volume of 1 ml) with the specific nominal volume being 1 ml, or may meet the outer diameter d1 (=6.85 mm±0.1 mm), inner diameter d2 (=4.65 mm±0.1 mm), and wall thickness s1 (•1.1 mm) of a 0.5 ml syringe (cf. ISO 11040-4, Tables 1 and B.1 for a nominal volume of 0.5 ml) with the specific nominal volume being 0.5 ml.

In these alternative cases, the barrel length is appropriately adjusted so as to ensure that the container 1100 provides the predetermined filling volume. Further, the above-mentioned flange portion put on top of the cylindrical barrel may form, in a circumferential direction, a continuous circular flange, e.g., in line with the flange of a conventional vial according to the ISO 8362-1 standard. The flange portion may be in line with a form B of a finger flange of a standardized syringe (cf. ISO 11040-4, FIG. 1, Form B). Additionally, the flange portion may be formed to comply, in terms of its cross-sectional shape, with relevant specifications of the above mentioned ISO 8362-1 standard. The flange portion may meet, in terms of its axial length/height, in terms of its upper inner edge, and/or in terms of its upper end surface, the relevant specifications as indicated in FIG. 1, FIG. 2, FIG. 3 and Table 1 of the ISO 8362-1 standard. Specifically, the axial length/height of the flange may amount to 3.6 mm±0.2 mm, the bevel angle of the upper inner edge may be approximately 45°, and/or the taper angle of the upper end surface of the flange may be 3°±2° (cf. ISO 8362-1, FIGS. 1 to 3).

Adopting the aforementioned length dimensions and angles may be useful in order to enable the flange portion of the container 1100 to cooperate with a conventional closure element as specified in the ISO 8362-2 standard. While the above-mentioned 3.6 mm±0.2 mm adopted from the ISO 8362-1 standard are preferable, the axial length/height of the flange portion may slightly differ from this standardized dimension as long as the flange portion still meets the following two functions: firstly, the flange portion shall enable handling and processing the container 1100 in conventional filling facilities and with conventional technology used for filling and processing of standardized syringes, i.e., the flange portion shall meet the function of a finger flange of a standardized syringe (cf. ISO 11040-4, FIG. 1); and secondly the design of the flange portion shall allow a tight closure of the container by using an appropriate closure element, e.g., a closure element according to the ISO 8362-2 standard of a conventional standardized vial. Further, the flange portion may differ, in terms of its inner diameter, outer diameter and its lower end surface, from the relevant specifications of the ISO 8362-1 standard (cf. ISO 8362-1, FIG. 1: diameter d4, diameter d2) in order to enable the flange portion to smoothly match the respective barrel dimensions. In particular, the flange portion may have a radially extending flat lower end surface unlike a standardized vial that has a tapered lower surface (cf. ISO 8362-1, FIGS. 1 to 3 showing a taper angle of 10°±5°). A flat lower end surface may facilitate the handling of the container in conventional filling facilities and with conventional technology used for filling and processing of standardized syringes. Generally, however, the lower end surface of the flange portion may be formed with a taper angle as it is known from ISO 8362-1 (cf. FIGS. 1 to 3 showing a taper angle of 10°±5°).

Accordingly, unlike a conventional vial, the container 1100, in particular if used as a primary packaging may have at its outer surface no such neck constriction as specified in the ISO 8362-1 standard (cf. ISO 8362-1, FIGS. 1 to 3: diameter d3, height h3). On the other hand, the inner surface of the container 1100 may be finished at the upper end, i.e., the upper end section opposite the flange portion, in line with the finish of any appropriate one of vial models A, B, or C of the ISO 8362-1 standard (cf. ISO 8362-1, FIGS. 1 to 3). Specifically, the inventive flange may at least be as thick as that of a standard prefilled syringe.

The closure element 1200 is accommodated within the container 1100 in a fluid-tight contact with the circumferential wall. In other words, the closure element 1200 is held by friction or in a force-locking manner within the container 1100. To this end, the closure element 1200 may preferably be formed so as to be elastically deformable. The closure element 1200, prior to being penetrated by the hollow needle 2122 in the process of delivery of the compounds stored in the container 1100, seals the container in a fluid-tight, compound-tight and aseptic manner by forming a leak-proof circumferential contact with its circumferential inner surface. Once the closure element 1200 has been penetrated by the penetration element, the closure element can be pushed by the penetration element 2100 against the frictional force towards the container bottom 1104 to displace and discharge the medical or pharmaceutical compound from the container 1100 into the hollow needle 2122. Accordingly, the penetration element 2100 may serve as a piston adapted to slide or move the closure element 1200 towards the container bottom 1104 to displace and discharge the medical or pharmaceutical compound from the container 1100 into the hollow needle 2122. The closure element 1200 is penetrated before it is moved towards the container bottom 1104. Specifically, the fluid-tight contact between an outer circumference of the closure element 1200 and the inner circumferential surface of the container 1100 is such that a force greater than a penetration force for penetrating the closure element is needed to move the closure element towards the container bottom 1104. Therefore, the closure element 1200 and the container 1100 together form a sort of slide-press-fit.

The closure element 1200 may have a through hole aligned with the hollow needle 2122 and closed on either one side by means of a sterility diaphragm. In such a case, as a matter of course, only the diaphragm has to be penetrated. Here "to penetrate" means to puncture or to pierce. The penetration element 2100 serves to penetrate the closure element 1200 and thereby to activate the delivery system 10 so as to enable the extraction and delivery of the compounds stored in the container 1100 and to extract the compounds. To this end, the extraction unit 2000 includes any kind of a penetration element that has, i.e., supports, holds and/or forms, a hollow needle. By penetrating the closure element 1200, the sterile storage of the compounds is undone at the point of penetration (and only there). Further, as mentioned above, the penetration element 2100 may serve to slide or move the closure element 1200 towards the container bottom 1104 in order to displace and discharge the medical or pharmaceutical compound from the container 1100 into the hollow needle 2122. The penetration element 2100 has an elongated structure with a cross-section smaller than a cross-section of the closure element 1200 and of the container 1100 in order to enable the penetration element 2100 to plunge or enter into the container.

Furthermore, the hollow needle 2122 may at least partially extend through a through-hole formed in the penetration element 2100. The hollow needle 2122 preferably extends to only such an extent into the penetration element 2100 that a safe support is assured or may extend completely through the through hole, projecting out of it or not at the other end of the penetration element 2100. The through hole in the former case is formed as a stepped hole, having a first portion accommodating the hollow needle 2122, and a second portion having a diameter essentially equal to the inner diameter of the hollow needle 2122 in order for a fluid channel formed within the penetration element 2100 to have an essentially constant diameter.

The hollow needle 2122 serves to penetrate the closure element 1200 and, to this end, protrudes, projects or juts out from an end face of the penetration element 2100 opposite or facing the container bottom 1104 parallel to and preferably aligned with the longitudinal axis A. The hollow needle 2122 is firmly held by the penetration element 2100, preferably extending into it by a predetermined amount assuring its firm position specifically in the process of penetration. The term hollow needle refers to the hollow needle 2122 used to penetrate the closure element 1200, whereas the term cannula used later refers to a hollow needle for application or administration of the compounds, which is arranged on the patient side, for example. The hollow needle 2122 may be made of metal or plastic, whereas the cannula is made of metal (standardized). The hollow needle 2122 may have at its lower end face a hole, or may have at a side of its lower end portion a hole or slit.

The link motion is defined between the first link motion portion 2112 and the second link motion portion 2118 of the extraction unit 2000 and is arranged in the extraction unit. The first link motion portion 2112 is provided at the penetration element 2100, while the second link motion portion 2118 is provided at the supporting element 2150 which is supported at the closure element 1200. One of the link motion portions may be provided with one of the projection 2132 and the guiding groove 2130, while the other of the link motion portions may be provided with the other of the projection 2132 and the guiding groove 2130. Because the supporting element 2150 is supported at the closure element 1200, the extraction unit 2000 as a whole is supported at the closure element. In other words, the inventive link motion is a form-locking connection that the first link motion portion 2112 forms with the second link motion portion 2118. The form-locking connection realized by the link motion between the first link motion portion 2112 and the second link motion portion 2118 prevents any unintended or accidental separation of the above-mentioned two parts of the extraction unit 2000, i.e., of the penetration element 2100 and the supporting element 2150.

The link motion is a detachable, unlockable or removable link or connection between the penetration element 2100 and the supporting element 2150.

Either of the penetration element 2100 or the supporting element 2150 can be provided with a slide block, i.e., a pin or peg, which is a projection that is moved along a predetermined trajectory by the guiding groove 2130 arranged in either the penetration element 2100 or the supporting element 2150. Thus, the inventive motion is not a screw joint. The term link motion is sometimes and synonymously called motion link. Both terms refer to a structure and not to a type of motion, as the first term might suggest. Specifically, the motion of one of the first and second link motion portions 2112, 2118 as a whole with respect to the other one of the first and second link motion portions follows the guiding groove 2130. This may be achieved if the projection 2132 as part of the one link motion portion is an element that is inflexible and steadfastly connected, preferably integrally connected, to a main body of the one link motion portion. Alternatively, the projection 2132 may in principle be flexibly connected to the main body of the one link motion portion in the way of any conventional ballpoint mechanism where a ballpoint refill is linearly movable while a projection of a compression piece thereof, usually activated by a thumb of a user to move the refill in and out, is flexible. Usually, in such a ballpoint mechanism, the compression piece is pressed once to move out the refill, and is removed in by pressing the compression piece a second time. Therefore, according to a preferred aspect of the present invention, the link motion may be designed in line with such a ballpoint mechanism. In the latter case, the first link motion portion 2112 (i.e., the penetration element 2100) may preferably be elastically biased relative to the second link motion portion 2118 (i.e., the supporting element 2150) in a direction opposite to the needle penetration direction. The needle penetration direction is the moving direction of the first link motion portion 2112, i.e., of the penetration element 2100 and of the hollow needle 2122, with respect to the second link motion portion 2118, i.e., the supporting element 2150, and the closure element 1200.

An elastic force biasing the extraction unit 2000 in a direction opposite to the penetration direction may be achieved by an elastic restoring force of the closure element 1200 while penetrating the closure element. Alternatively, the elastic force may be achieved by providing an elastic element, such as a compression spring 2120, between the penetration element 2100 and one of the supporting element 2150, container 1100 or closure element 1200, or in functional terms between the first link motion portion 2112 and second link motion portion 2118. The elastic element is disposed between an end surface of the penetration element 2100 that faces the closure element 1200 and the supporting element 2150 or closure element. The elastic element accommodates the hollow needle 2122 projecting from the end surface of the penetration element 2100. The shape of the guiding groove 2130 and, therefore, the trajectory of the projection 2132 is not limited in any way. The guiding groove 2130 may generally have the shape of a regular spiral, i.e., a helical curve, or may be curved in any other way, or may be just straight, or may form spiral, curved and/or straight guiding groove sections. In other words, the guiding groove 2130 may extend linearly along and/or rotationally around the longitudinal axis A so as to define a predetermined way of movement of the projection 2132, which extends linearly along and/or rotationally around the longitudinal axis A. A straight guiding groove is the simplest form of a guiding groove and nevertheless has the advantage that the penetration element 2100 cannot be retracted once the closure element 1200 has been penetrated. Therefore, the delivery system 10 can be depolluted as a whole, without the danger of contaminating something with its former compounds.

The penetration element 2100 is disposed within and longitudinally guided by the supporting element 2150. The supporting element 2150 surrounds at least the first link motion portion 2112 of the penetration element 2100. Therefore, the supporting element 2150 participates in assuring a well defined spatial relationship of the penetration element 2100 and the hollow needle 2122 with respect to the closure element 1200. The first link motion portion 2112 is inserted into the second link motion portion 2118.

Figure 1B:
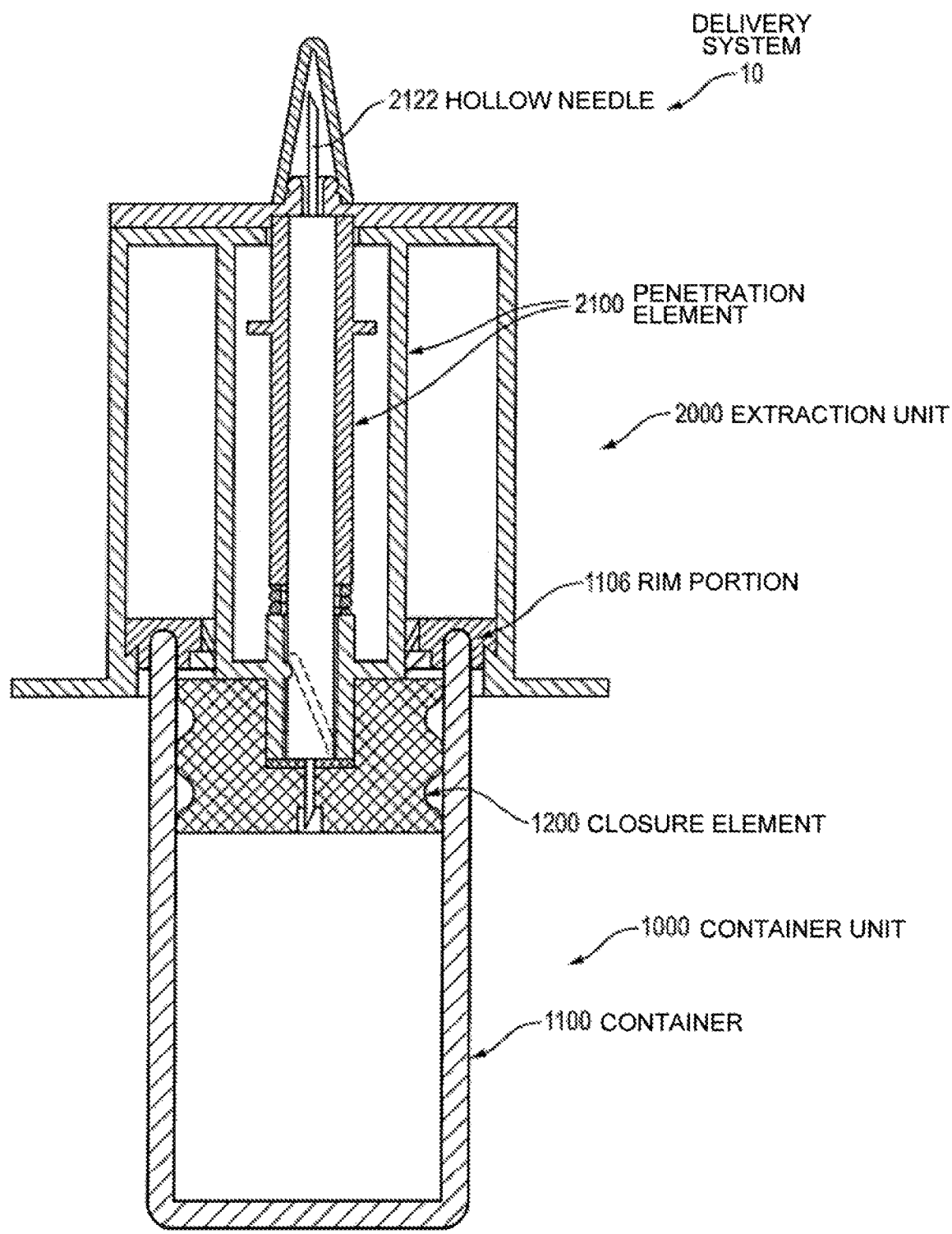
FIG. 1B is a schematic drawing of the delivery system of FIG. 1A in an intermediate state.
Figure 1C:
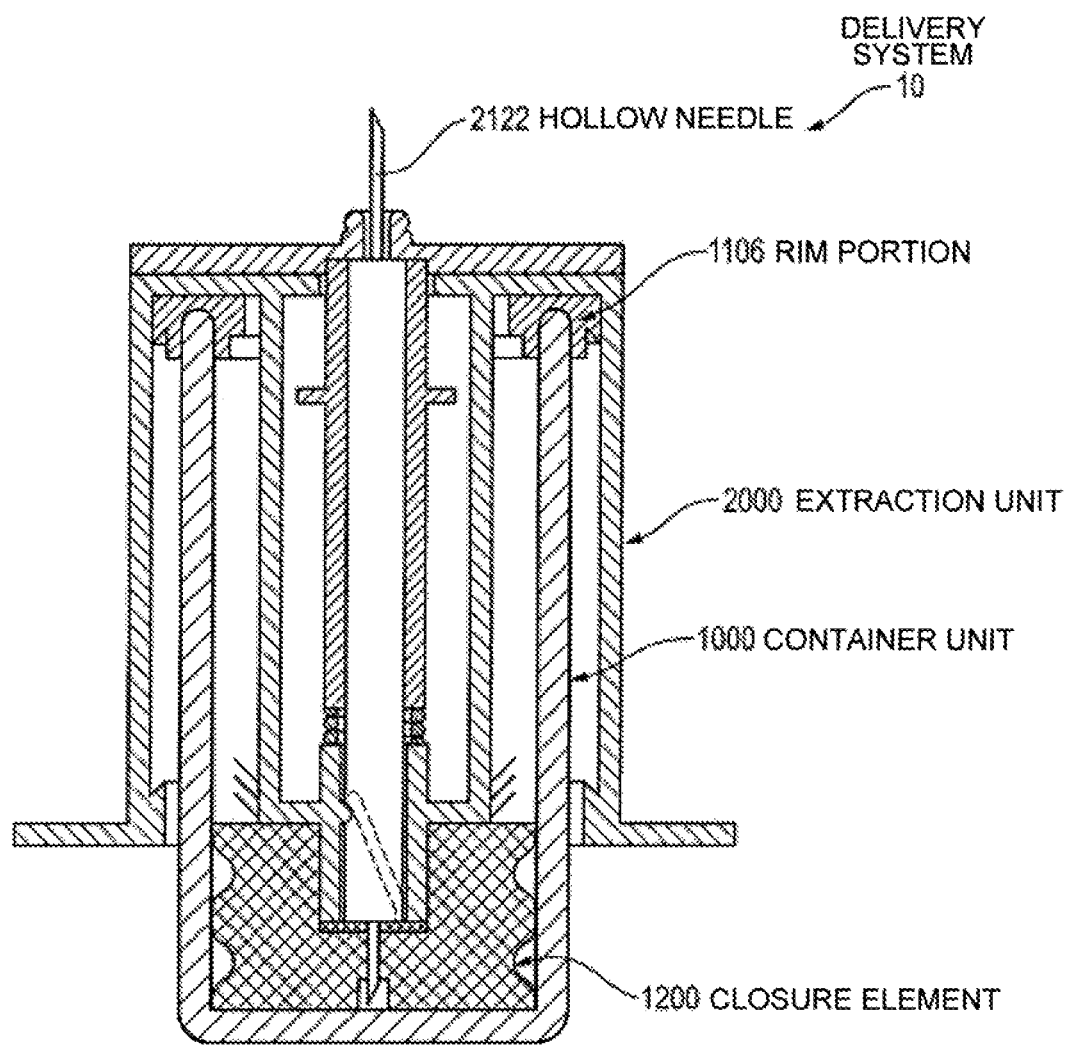
FIG. 1C is a schematic drawing of the delivery system of FIG. 1A in a final state.

The second link motion portion 2118 is formed as a corresponding recess or blind hole provided in the supporting element 2150 so as to receive the first link motion portion 2112 projecting from the penetration element 2100. In the broadest sense, the delivery system 10 merely requires the link motion to be formed between the first and second link motion portions 2112, 2118. Because any link motion composed of two components implies that one of these is inserted into the respective other one, the aforementioned aspect defines a specific spatial relationship as shown in FIGS. 1A to 1C. Alternatively, the supporting element 2150 may be formed so that the second link motion portion 2118 projects towards the penetration element 2100 and is inserted in a corresponding recess formed in the penetration element 2100 and forming the first link motion portion 2112. In both cases, the projection 2132 or the guiding groove 2130 can be in either one of the first or second link motion portions 2112, 2118.

The extraction unit 2000 also includes a mounting element 2200 that is connected, preferably integrally, to the penetration element 2100 or to the supporting element 2150. The extraction unit 2000 is engaged, preferably releasably, with a rim portion of the container 1100 that defines the open second end. The mounting element 2200 assists in supporting and holding the extraction unit 2000 at the container unit 1000. The mounting element 2200 accommodates the penetration element 2100. The mounting element 2200 may surround the penetration element 2100 and may be the component of the extraction unit 2000 that connects the extraction unit to the container unit 1000 by being connected to the rim portion. Therefore, the mounting element 2200 may participate in assuring a well-defined spatial relationship between the penetration element 2100 (and therefore also the hollow needle 2122) and the container unit 1000 and the container proper. The rim portion of the container unit 1000 is a ring-shaped portion that includes a circular end portion along the open second end of the container 1100 (independent of the shape of the circular end portion), and may include more than one separate element.

The container 1100 includes a flange as a part of the rim portion. The rim portion may be formed to have the flange. The flange may be considered to be the aforementioned flange portion. The term flange refers to the container proper, while the term flange portion may be thought of as an extended flange and may include, besides the flange proper of the container 1100, an attachment element 1114. The flange portion can be associated with the rim portion.

The shape of the rim portion may vary. The rim portion as part of the container 1100 may be a flange, i.e., a circular disc-shaped protrusion extending outwardly, preferably radially outwardly, from the open second end. Alternatively, the ring may be structured to have one or more steps or one or more undercuts in cross-section. The rim portion may include an attachment element 1114 fitted onto the container 1100 at the open second end, and the extraction unit 2000 is engaged with the attachment element.

The attachment element 1114 may serve to connect or mount the extraction unit 2000 to the container 1100. The attachment element 1114 may be regarded as an adapter. The attachment element 1114 also provides the function of dimensional adaptation allowing the design to be individually (i.e., of the container 1100 as well as of the mounting element 2200) optimized to some extent. Nevertheless, the attachment element 1114 is regarded here as part of the container unit 1000, specifically of its rim portion. The rim portion of the container unit 1000 includes a rim portion of the container proper together with the attachment element 1114. The attachment element 1114 aligns the extraction unit 2000 and the hollow needle supporting means 2110 with respect to the container unit 1000. The attachment element 1114 together with the second link motion portion 2118 plug into the closure element 1200 and serve as a guide in the process of attachment of the extraction unit 2000 to the container unit 1000 and in the process of penetration of the closure element 1200 by the hollow needle 2122.

The attachment element 1114 is formed as a ring-shaped cap surrounding the supporting element 2150. The attachment element 1114 may surround the first and the second link motion portions 2112, 2118. The supporting element 2150 and the penetration element 2100 may extend through an opening (preferably central) of the attachment element 1114. The attachment element 1114 is part of the rim portion of the container 1100.

The attachment element 1114 has a first overlapping portion outwardly overlapping the rim portion. The attachment element 1114 has a second overlapping portion inwardly overlapping the rim portion. In a longitudinal section including the longitudinal axis A of the container 1100, the attachment element 1114 may overlap the rim portion in a U-shape in case of inwardly and outwardly overlapping the rim portion, where the legs of the U (the l-portions thereof) may be of equal or different length. The mounting element 2200 has the shape of a cup overlappingly engaged in an invertably arranged manner with respect to the container unit 1000 with the rim portion. The supporting element 2150 is attached to and protrudes centrally from a mounting element bottom of the mounting element 2200 and accommodates and longitudinally guides the penetration element 2100.

The penetration element 2100, supporting element 2150, cup-shaped mounting element 2200 and hollow needle 2122 are essentially rotation-symmetrically arranged with respect to the longitudinal axis A. Cup-shaped is to be understood as essentially equally shaped as the container 1100, i.e., preferably right-cylindrically, preferably of circular cross-section, preferably with the mounting element bottom flat. Invertably arranged as used herein means that the attachment of the extraction unit 2000 to the attachment element 1114, or generally to the rim portion, by means of the mounting element 2200 may be thought of as putting the former in an upside-down fashion with respect to the container 1100 over the latter. Therefore, centrally protruding means protruding from a central portion of the mounting element bottom into an inner space defined by the mounting element 2200 and towards the bottom of the container 1100. At least one of an edge portion of the mounting element 2200 and the rim portion is deformable in a direction orthogonal to the longitudinal axis A for the extraction unit 2000 to be snappably engageable with the rim portion in a mounting process of the delivery system 10.

In the attached state, the ring-shaped open end portion or edge portion of the cup-shaped mounting element 2200 together with the ring-shaped attachment element 1114 or rim portion form a circular press-fit in which the deformation is such that the former is expanded or stretched and/or the latter is compressed. The deformation state of the former and/or the latter is largest in the process of attachment, and is smallest but not zero in the final attached state. In the final attached state, the mounting element 2200 is snappably attached or form-lockingly connected by engagement of the cup-shaped mounting element into an undercut of the attachment element (rim portion).

In order to be deformable, the mounting element 2200 is made of an elastic material and/or is slitted. Therefore, the deformation mentioned above can be achieved either by an elastic formation that is based on the material only, and/or by elastic formation applied to a structure that allows portions of the mounting element 2200 to be separated by a slit. The mounting element 2200 may have a slitted structure in which one or more slits extend from the open end (edge portion) towards the mounting element bottom. A plurality of slits are formed, preferably in equal intervals, along the circumference of the mounting element 2200.

The mounting element 2200 may include a sort of lamella structure with lamellas 2144 pointing downwards towards the container bottom 1104. These lamellas 2144 are flexibly pivotable about their respective fixation point to be able to circumferentially expand in the process of mounting the mounting element 2200 to the container unit 1000. The mounting element 2200 and the rim portion are provided with complementarily shaped engagement means that are engaged with each other in a snapped-in engagement state. The engagement means forms a hook-hook-pair in which each of the hooks is circularly shaped. The engagement means may alternatively not be complementarily shaped. For example, one of the portions may be a (circular) hook, while the other portion may be a (circular) groove adapted to fixedly accommodate the hook, thereby forming a hook-groove-pair.

The penetration element 2100 has a delivery end formed as a part of a Luer lock connector. The Luer lock connector is a preferred design because of its standardization. The Luer lock connector connects the delivery system 10 to another device or to a human body or the body of an animal. The part of a Luer lock connector that is part of the delivery system 10 may be formed as either the female or the male part thereof.

The penetration element 2100 has a delivery end formed as a spray valve in which the means has no cannula. Instead, the blunt end portion of the hollow needle 2122 (the end portion opposite to the lower sharp end portion) transitions or blends into the spray valve. The blunt end portion of the hollow needle 2122 is formed as the spray valve. Alternatively, the spray valve is a separate component attached to or inserted into the channel formed in or extending through the penetration element 2100. The spray valve is recessed or set back into an upper or outer surface of the mounting element 2200 in order not to protrude therefrom.

In another embodiment, the penetration element 2100 has a delivery end formed as a cannula. A cannula is a hollow needle adapted to be plugged on a syringe to put a medical fluid into a human being or an animal, mostly intravenously. Preferably, the cannula is of a type that allows the use of the delivery system 10 as an infusion system. For example, the cannula allows a flow of air into the container 1100 and, thereby, a flow of the compounds out of the container solely by gravitation. The term "to extract" used above may in this case be replaced by "to empty" in view of the passive draining of the compounds, i.e., the draining without the help of some kind of actuator. The hollow needle 2122 and the cannula are preferably integrally formed as one piece. In such a case, the above terms refer to portions of a hollow double-needle. The hollow needle 2122 has a tapered, beveled or chamfered tip to allow for an easy penetration of the closure element 1200.

The delivery system 10 may further include a protecting cap covering a delivery end of the penetration element 2100. The cap may be movably attachable to a rotating element and removably connected to the penetration element 2100. Contact surfaces of the container bottom 1104 and the closure element 1200 are complementarily shaped, and at least one of the contact surfaces includes a blind hole for accommodating a tip of the hollow needle 2122. A force along the longitudinal axis A is allowed to be transmitted from the penetration element 2100 to the closure element 1200 in order to move the closure element towards the container bottom 1104. The term complementarily shaped means that opposing surfaces of the closure element 1200 and the container bottom 1104 are configured such that they are essentially in surface contact with each other when the assembly of the penetration element 2100 and the closure element 1200 is located at its most downward position (i.e., when the compounds initially contained in the container 1100 have been extracted as much as possible with the hollow needle 2122 in a complete extraction allowing position). As used above, "essentially" means except for the blind hole (depression or recession) that is formed in one or both of them. Thus, the contact surfaces are essentially parallel to each other (except for the blind hole). Any convexity of one of the contact surfaces corresponds to the concave mirror image of the other one of the contact surfaces. Allowing a force along the longitudinal axis A to be transmitted from the penetration element 2100 to the closure element 1200 causes the penetration element to be inserted as deep as possible into the closure element 1200, i.e., up to a position where respective end faces are in contact with each other. Up to that position, which may be called a longitudinal force transmittable position, the closure element 1200 is held by friction between its circumferential surface and an inner surface of the container 1100 and, therefore, not moved towards the container bottom 1104 but only penetrated by the hollow needle 2122.

The contact surfaces are generally flat-shaped or ellipsoidically or spherically shaped. The shapes of the contact surfaces are variations in terms of their respective manufacturing process as well as for the extraction efficiency they allow. Nevertheless, the contact surfaces may be shaped arbitrarily. Preferably, the ellipsoidically or spherically shaped contract surfaces are disposed such that their respective axis of symmetry is aligned with the longitudinal axis A.

The penetration element 2100 may be elastically biased in a direction away from the supporting element 2150. The direction away from the supporting element 2150 is a direction opposite to the needle penetration direction. In this regard, there may be an elastic element arranged between the penetration element 2100 and one of the supporting element 2150, the container 1100 or the closure element 1200.

The needle penetration direction is the moving direction of the first link motion portion 2112 (hollow needle) with respect to all other components of the delivery system 10. For example, the needle penetration direction is the direction of the first link motion portion 2112 with respect to the second link motion portion 2118 when the first link motion portion 2112 is rotated in order make the hollow needle 2122 penetrate the closure element 1200. This direction is referred to herein as a forward direction. The movement of the first link motion portion 2112 in the needle penetration direction is carried out against the elastic force of the elastic element, which itself is a compression spring. The elastic element may be provided between the penetration element 2100 and an end surface that faces the closure element 1200 and either the supporting element 2150 or the closure element 1200.

The elastic element accommodates the hollow needle 2122 projecting from the end surface of the penetration element 2100. In this case, the elastic element surrounds a core portion of the first link motion portion 2112 having the longitudinal axis A as a symmetry axis from which the hollow needle 2122 projects. The first link motion portion 2112 includes a bush portion surrounding the core portion in which the bush portion has a flange-shaped stopping element (flange) that is pressed against the mounting element 2200 by means of the elastic element to hold the first link motion portion 2112 in that position until it is intentionally rotated. The intentional rotation is carried out by means of a rotating element manipulated by a user.

The supporting element 2150 includes a tubular body coupled to the closure element 1200. The tubular body forms the second link motion portion 2118.

The penetration element 2100 includes lamellas 2144 extending from its outer circumferential surface in a slanting upward direction and engaged with the container unit 1000. The lamellas 2144 are adapted to prevent the detachment of the penetration element 2100 from the rim portion. The lamellas 2144 advantageously have the shape of lateral areas of frustums or truncated cones arranged in succession or in a row along the longitudinal axis A with preferably different pitch angles with respect to the longitudinal axis. The lamellas 2144 are directed slantingly upward or diagonally upward in order to be able to act as hooks preventing the detachment of the extraction unit 2000 from the attachment element 1114, i.e., any movement of the extraction unit 2000 in the above defined retraction direction or backward direction. The term preventing means making such movement impossible (without damaging the system) or impeding or hampering such movement.

The guiding groove 2130 extends linearly along and/or around (i.e., rotationally around) the longitudinal axis A. The guiding groove 2130 may be such that a relative movement of the first link motion portion 2112 with respect to the second link motion portion 2118 is carried out by (i) rotating and/or advancing the first link motion portion 2112 along the longitudinal axis A to longitudinally move the hollow needle 2122 by a first distance (h2) to make the hollow needle penetrate the closure element 1200, and (ii) further rotating and/or retracting the first link motion portion 2112 to longitudinally move the hollow needle by a second distance (h2−h1) to retract the hollow needle to a complete extraction allowing position.

The complete extraction allowing position is a position that allows the extraction of essentially all of the compounds stored in the container 1100 to be extracted. First of all, this position is determined in that, in the penetration process, the hollow needle 2122 has to completely penetrate the closure element 1200. Depending on the structure of the closure element 1200, the closure element has to be over-penetrated to some extent. In the case of a diaphragm, the diaphragm may be stretched and spring back. This over-penetration position is the position achieved by the first distance (h2). In this embodiment, the hollow needle 2122 is then retracted to the complete extraction allowing position (as for terminology, the over-penetration position may be called a complete penetration position). This position is achieved by the second distance (h2−h1, with h1<h2). Where the closure element 1200 is fully moved towards the bottom in the process of delivery, the retraction prevents a contact of the tip of the hollow needle 2122 with the bottom and, as a consequence, a space between the closure element 1200 and the bottom. Such a space, in the case of a protruding hollow needle, would prevent the compounds included therein to be extracted. Where the closure element 1200 is not moved towards the bottom in the process of gravitation delivery, the container 1100 is held in an inverted position compared to the previous variation. In such a case, the retraction of the hollow needle 2122 assures that the hollow needle does not extend above a residual amount of compounds.

The guiding groove 2130 may further be formed such that a relative movement of the first link motion portion 2112 with respect to the second link motion portion 2118 is further carried out by (iii) rotating the first link motion portion 2112 to a longitudinal locking position, preferably without any further longitudinal movement of the hollow needle 2122. The longitudinal locking position is a position in which the first link motion portion 2112 is longitudinally fixed. In the embodiment in which the closure element 1200 is to be moved, this position may also be called a longitudinal force transmittable position that allows a longitudinal force, i.e., a force along the longitudinal axis A, sufficient to move the closure element 1200 to be applied.

Thus, in a form-locked state, the penetration element 2100, i.e., the extraction unit 2000, is secured to the closure element 1200 and is adapted both to piston-like push and pull the closure element. The pulling ability allows any remaining amounts of the compounds that inevitably remain in the system after administration to be drawn back and thereby avoids spilling these amounts when the extraction unit 2000 is removed from the container 1100 after having delivered the compounds.

The delivery system 10 may form a modular system comprising the extraction unit 2000 as a first module and the container unit 1000 as a second module. The two modules can be exchanged in case one of them is damaged or in case differently shaped containers and/or containers storing different compounds are to be used or in case one of them is to be cleaned, as long as they are correspondingly shaped to be connectable. A user may order only a single first module used for a plurality of different compounds. In such a case, the first modules, specifically the extraction unit 2000, may be sterilizable. The second module may include the container 1100, the attachment element 1114, and the closure element 1200 as a first, a second, and a third sub-module, respectively. This division into first and second modules can be extended. The division into first and second modules demonstrates the modular concept of the present invention. At least one of the modules may be sterilizable.

FIG. 1A is a schematic drawing showing an initial state of a delivery system 10 according to a preferred embodiment of the present invention. The delivery system 10 includes a container unit 1000 and an extraction unit 2000. The container unit 1000 includes a container 1100 and a closure element 1200. The container 1100 has a hollow right-cylindrical shape with a tube-shaped side wall 1102 and a container bottom 1104 closing the side wall 1102 at a lower first end. The side wall 1102 has a ring-shaped upper end or rim portion 1106 that defines an upper and open second end. The side wall 1102 also has an inner surface 1108 and an outer surface 1110.

The rim portion 1106 includes an attachment element 1114 that is a generally ring-shaped, cap-like adapter. The attachment element 1114 is provided with a through hole 1118 and is formed in such a way that the element straddles the rim portion 1106 of the container 1100. A ring-shaped inner portion 1120 stretches longitudinally (along the longitudinal axis A) essentially equally along the inner surface 1108 of the container 1100 towards the container bottom 1104 as a ring-shaped outer portion 1122 extends along the outer surface 1110 of the container 1100. The inner and outer portions 1120, 1122 define a circular groove 1124 with a circularly extending half-pipe-like roof (or bottom, when regarded upside-down compared to FIG. 1A, so that the groove forms a circular trough with walls of equal wall heights). Therefore, a lower surface 1126 of the attachment element 1114 includes an outer ring-shaped end face 1128, an inner ring-shaped end face 1130, and a surface 1132 of the roof. The circular groove 1124 serves to accommodate a rim portion 1142 of the barrel of the container 1100. The attachment element 1114 includes a circular detent 1134 extending outwardly and downwardly along an outer portion 1122 and the rim portion 1142, i.e., in a slanting downward direction.

The through hole 1118 has a stepped structure with a lower portion 1136 having a larger diameter than an upper portion 1138. Thus, the upper portion 1138 forms a ring-shaped nose extending radially inwardly.

The closure element 1200 is formed from an elastic material and is accommodated within the container 1100 in fluid-tight contact with the container to be adapted to seal the container 1100 until delivery of the compounds stored therein. To improve the sealing property, an outer surface 1202 of the closure element 1200 that is in contact with the inner surface 1108 of the side wall 1102 of the container 1100 has a ribbed structure with a plurality of circular ribs 1204. The closure element 1200 has a larger blind hole 1206 that is open in the direction away from the container bottom 1104 and arranged centrally, i.e., symmetrically with respect to the longitudinal axis A of the container, which coincides with the longitudinal axis of the delivery system 10. The closure element 1200 has a smaller blind hole 1208 also arranged centrally, but open in the direction of the container bottom 1104. The smaller blind hole 1208 is smaller than the larger blind hole 1206 both in terms of depth and in terms of width. As shown in FIG. 1A, a central/axial thin wall portion 1210 of the closure element 1200 is disposed between the larger blind hole 1206 and the smaller blind hole 1208.

The extraction unit 2000 includes a supporting element 2150, a penetration element 2100, a mounting element 2200 and a rotating element 2300. The penetration element 2100 includes a hollow needle supporting means 2110. Further, as shown in FIGS. 1A-1C, the penetration element 2100 has an elongated structure with a cross-section smaller than the cross-section of the closure element 1200 and of the container 1100 in order to fit into the container 1100.

The hollow needle supporting means 2110 of the penetration element 2100 includes a first link motion portion 2112 and a hollow needle 2122. The first link motion portion 2112 has a core portion 2114 and a bush portion 2116 integrally formed with the core portion 2114 and completely surrounding the core along an upper part of the length of the core. The supporting element 2150 includes a second link motion portion 2118 adapted to accommodate a lower part of the core portion 2114. As shown in FIG. 1A, an elastic element in the form of a compression spring 2120 is arranged between the penetration element 2100 and the supporting element 2150. In order to provide the desired function, the elastic element 2120 generally serves to bias the first link motion portion 2112 with respect to the second link motion portion 2118. Alternatively, the compression spring 2120 can be arranged between the lower end face 2134 of the core portion 2114 and a circular upper surface 1212 of the closure element 1200 (with a diaphragm 2140 arranged between them). The compression spring 2120 can also be positioned between a ring-shaped surface formed around the second link motion portion 2118 and the flange 2128, or between any other structures formed at the first and second link motion portions and adapted to receive the force applied by the compression spring 2120 to bias the first and second link motion portions away from each other.

The compression spring 2120 is wound around the core portion 2114 between a lower end face 2126 of the bush portion 2116 and an upper end face 2124 of the second link motion portion 2118 or of the supporting element 2150. The compression spring 2120 biases the penetration element 2100 with the first link motion portion 2112 in a direction away from the supporting element 2150 with the second link motion portion 2118, i.e., upwards or in a direction opposite a needle penetration direction. The bush portion 2116 includes a flange 2128 at its outer surface that is pressed in the initial state shown in FIG. 1A against the mounting element 2200. A guiding groove 2130 is formed in a surface of the lower part of the core portion 2114. The guiding groove 2130 is an engaging portion of the first link motion portion 2112.

The second link motion portion 2118 includes a projection 2132 formed at its inner surface. The projection 2132 is adapted to become engaged with the guiding groove 2130 to form a link motion adapted to move the penetration element 2100 relatively to the supporting element 2150 by rotating the first link motion portion 2112 relative to the second link motion portion 2118 by means of the rotating element 2300 that is torque-proof fitted onto an upper end portion of the first link motion portion 2112.

The hollow needle 2122 has a lower, chamfered end portion extending downward beyond a lower end face 2134 of the core portion 2114, and an upper, chamfered end portion extending upward beyond an upper end face 2136 of the first link motion portion 2112. Thus, the hollow needle 2122 has a cannula portion extending upward out of the hollow needle supporting means 2110.

The supporting element 2150 has the form of a cup that includes a right-cylindrical side wall 2152 connected with its upper end face to the mounting element 2200, and a supporting element bottom 2124 at its lower end. The supporting element bottom 2124 has a central through hole 2156 through which the second link motion portion 2118 extends. The outer surface of the second link motion portion 2118 is connected, at an approximate central position in the direction of the longitudinal axis A, to a rim portion of the through hole 2156. In the preferred embodiment, the second link motion portion 2118 is formed integrally with or is integrally attached to the supporting element 2150, as seen in FIG. 1A.

The supporting element 2150 is supported at the closure element 1200 in a longitudinal direction, as shown in FIG. 1A. The supporting element 2150 is coupled to the closure element 1200 via the lower part of the second link motion portion 2118 being accommodated in a form- and force-locking manner within the larger blind hole 1206 of the closure element 1200. The mounting element 2200 has the form of a cup that includes a side wall 2204 and a mounting element bottom 2202 at its upper first end.

The side wall 2204 has a ring-shaped lower end portion or rim portion 2206 defining a lower and open second end of the mounting element 2200. The mounting element 2200 is invertedly and partly overlappingly arranged with respect to the container 1100. The mounting element 2200 is provided with a finger flange 2208 extending outwardly along the rim portion 2206. The mounting element 2200 is further provided with a circular detent 2210 extending inwardly and upwardly, i.e., in a slanting upward direction, along the rim portion 2206. The mounting element bottom 2202 has a circular opening through which the first link motion portion 2112 extends upwardly, and along an edge of which the flange 2128 makes abutting contact opposing the force of the compression spring 2120. The lower part of the second link motion portion 2118 protruding from a lower end face of the supporting element 2150 forms a needle space 2138 that extends downward into the larger blind hole 1206 and is aseptically sealed by the diaphragm 2140 attached to a lower, ring-shaped end face 2142 of the second link motion portion 2118.

The end face 2142 is in contact with the circular upper surface 1212 of the closure element 1200, with the diaphragm 2140 arranged between face 2142 and surface 1212. Lamellas 2144 are disposed at a lower outer surface of the supporting element 2150 and extend upward and outward away from the supporting element 2150. The lamellas 2144 engage with the ring-shaped nose of the attachment element 1114 in order to allow the supporting element 2150 of the penetration element 2100 to easily move downward with respect to attachment element 1114 and in order to impede any movement in the opposite direction.

The detents 1134 and 2210 form circular hooks that fittingly engage with each other in the attached initial state shown in FIG. 1A. The rotating element 2300 is removably or non-removably fitted in a torque-proof way onto the hollow needle supporting means 2110 and includes a central hole 2301 penetrated by the cannula portion of the hollow needle 2122. The cannula portion of the hollow needle 2122 is protected by a protective cap 2302.

FIGS. 1A to C show various stages or steps of the delivery of the pharmaceutical compounds stored in the container 1100.

Figure 2A:
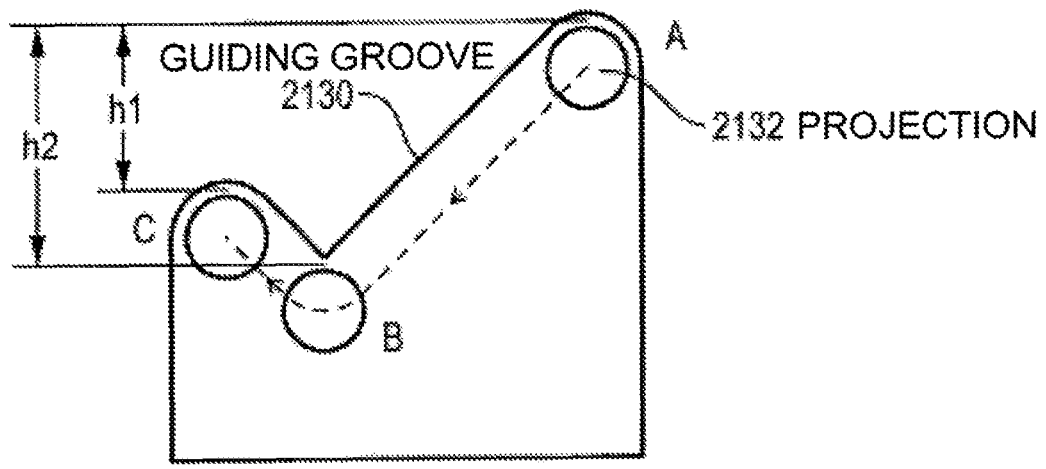
FIG. 2A is a schematic drawing of developed surfaces of a link motion of a first variation of the delivery system according to the present invention.

FIG. 2A shows a developed view of a preferred first variation of the link motion guided by the projection 2132 following along the guiding groove 2130. In the developed view, the projection 2132 and the guiding groove 2130 may be part of the core portion 2114 and the second link motion portion 2118, respectively, or vice versa. That is, in FIG. 2A, the projection 2132 shown may be part of the core portion 2114 or part of the second link motion portion 2118. The same holds correspondingly for the guiding groove 2130. According to FIG. 2A, after the projection 2132 is inserted into the guiding groove 2130 at point A, hereafter called the starting position, the projection 2132 is moved along the guiding groove 2130 by rotating the core portion 2114 with respect to the second link motion portion 2118 first downwards by a longitudinal distance h2 to a position B and then upwards by a longitudinal distance h2−h1 to a position C. Both distances h1 and h2 are measured longitudinally with respect to the starting position, as shown in FIG. 2A.

Figure 2B:
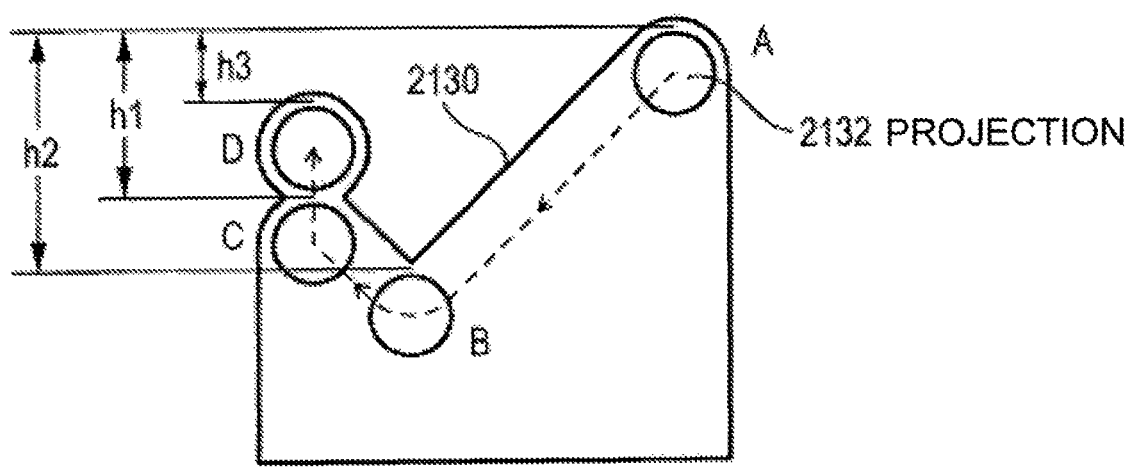
FIG. 2B is a schematic drawing of developed surfaces of a link motion of a second variation of the delivery system according to the present invention.

FIG. 2B shows a developed view of a preferred second variation of the motion link defined by the projection 2132 following along the guiding groove 2130. The second variation differs from the first variation in that position D is added. Position D is displaced with respect to position C radially and/or longitudinally with respect to the longitudinal axis A. Position D (>h3) is achieved by further relatively rotating the core portion 2114 with respect to the second link motion portion 2118, and is a locking position allowing a longitudinal force to be exerted on the extraction unit without return-moving the projection 2132 back to position B in the process of pushing the closure element 1200 downwards. As shown in FIG. 2B, h3<h1<h2.

Figure 3A:
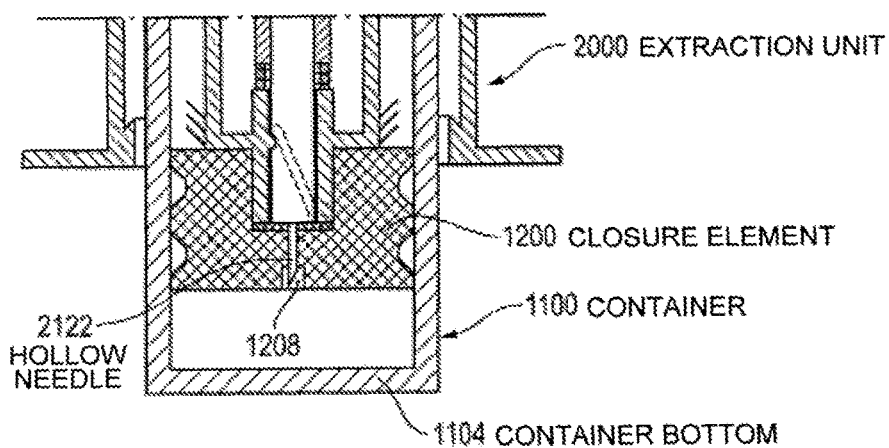
FIG. 3A is a schematic drawing showing a first variation of the shape of a closure element and a container bottom of the delivery system according to the present invention.
Figure 3B:
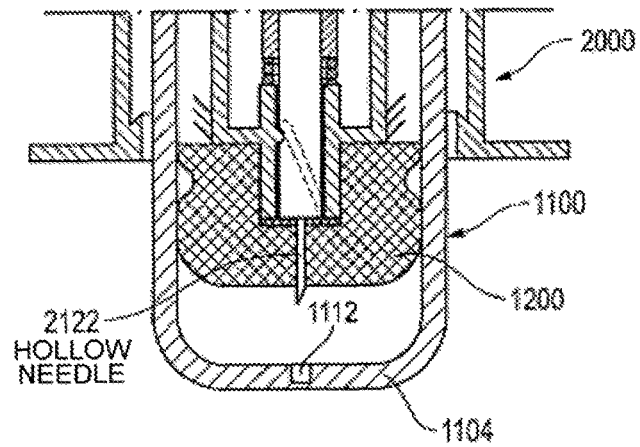
FIG. 3B is a schematic drawing showing a second variation of the shape of the closure element and the container bottom.
Figure 3C:
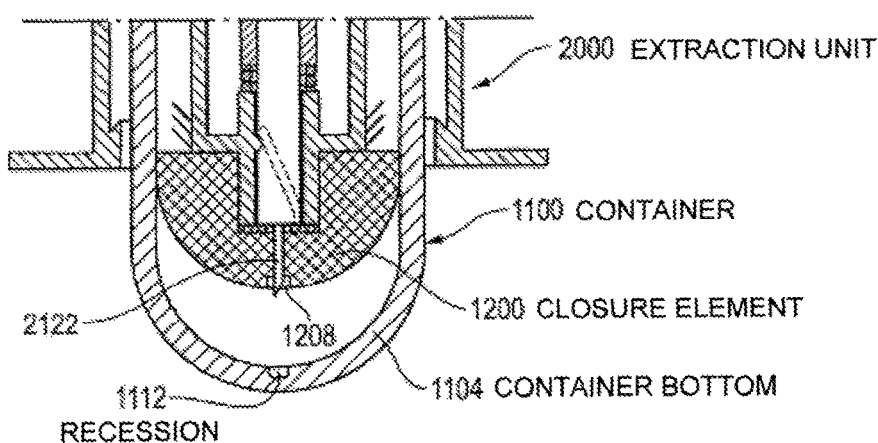
FIG. 3C is a schematic drawing showing a third variation of the shape of the closure element and the container bottom.

FIGS. 3A-3C illustrate various corresponding shapes of the closure element 1200 and the container bottom 1104. The shapes of the contact surfaces of the closure element 1200 and the container bottom 1104 correspond to each other in that any convex shape of the former is equivalent to the concave shape of the latter. The contact surfaces shown are either both flat (FIG. 3A), convex (closure element 1200) and concave with flat surfaces but rounded edges (FIG. 3B), or spherical (FIG. 3C). The surface shapes are designed to ensure that the remaining compounds are minimized when the closure element 1200 is in contact with the container bottom 1104 by channeling the compounds towards the hollow needle 2122 immediately prior to the contact of the contact surfaces. Therefore, the inverse case, namely that the closure element 1200 has a concave lower surface and the container bottom 104 bulges convexly upwards, does not achieve this goal.

The purpose of the smaller blind hole 1208 is, firstly, to accommodate and protect the hollow needle 2122 from damage and, secondly, to allow an immediate contact of the contact surfaces to reduce to a minimum the amount of the compounds that cannot be extracted from the container 1100. As shown in FIGS. 3A-3C, there are various alternatives to this end. The smaller blind hole 1208 may be provided in only one of the surfaces, such as in the closure element 1200 (FIG. 3A) or in the container bottom 1104 (FIG. 3B), or a blind hole can be made in both surfaces (FIG. 3C). FIGS. 3B-3C show that the container bottom 1104 may be provided with a recession 1112. In view of the functions of the smaller blind hole 1208 and the recession 1112, it is evident that in the case of FIG. 3C, these can be dimensioned smaller than in the cases of FIGS. 3A-3B.

FIG. 4 shows an enlarged detailed schematic view of an alternative container 1100 that has a flange 1140 extending outwardly along its rim portion 1142 (the rim portion of the container proper or barrel). The flange 1142 is accommodated within a circular groove 1144 of an alternative attachment element 1114'. In the process of attaching the attachment element 1114' to the container 1100, the attachment element 1114' is stretched and snapped over and around the flange 1140. The attachment element 1114 is shown very schematically and simplified in FIG. 4 to emphasize the position of the circular groove 1144. The actual alternative attachment element 1114' is identical in all other structural terms with the attachment element 1114.

FIGS. 5A-5B are schematic drawings illustrating an alternative of a link motion. In this embodiment, the projection 2132 is flexibly connected to a main body of one of the first or second link motion portions, here either the core portion 2114 (case shown in FIGS. 5A-5B) or the supporting element 2150 (numerals in brackets in FIGS. 5A-5B). The projection 2132 is connected by means of a flexible bar 2158, while the guiding groove 2130 is formed in the respective other one of the first or second link motion portions, here the core portion 2114 or the supporting element 2150. The arrows in FIG. 5A show that the flexible bar 2158 is allowed to pivot essentially circumferentially or tangentially with respect to a circumference of the main body in a plane perpendicular to the longitudinal axis about a connection point 2160. The flexible bar 2158 is integrally connected to the main body at the connection point 2160. The guiding groove 2130 may have the shape shown in FIG. 5B, resulting in a link motion as known in principle from a ballpoint pen where the refill cartridge (corresponding to the penetration element 2100) is only linearly movable (here along the longitudinal axis A), while a projection of a compression piece (corresponding to the extraction unit 2000), usually activated by the thumb of the user to move the refill cartridge in and out, is flexibly suspended (corresponding to the attachment of the projection 2132 by means of the flexible bar 2158). In the present invention, as in a similar type of link motion mechanism of a ballpoint pen, the extraction unit 2000 (ballpoint pen compression piece) is pressed a first time (here moved downwards) to advance and retract the hollow needle 2122 (ballpoint pen refill cartridge) (cf. FIG. 5B), and is pressed a second time to move in the refill.

Figure 5C:
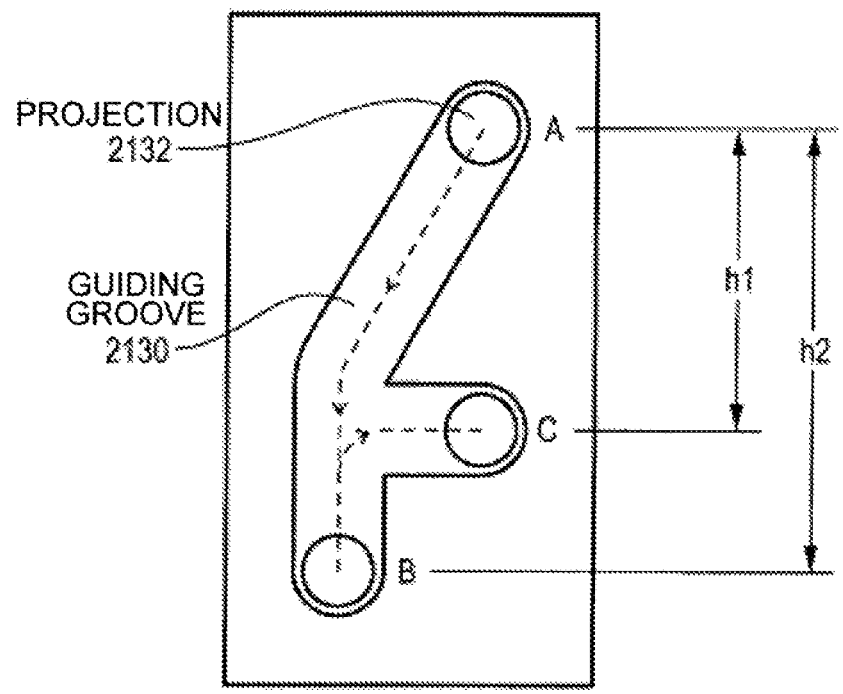
FIG. 5C is a schematic drawing illustrating a first modification of the alternatives of FIGS. 5A and 5B.
Figure 5D:
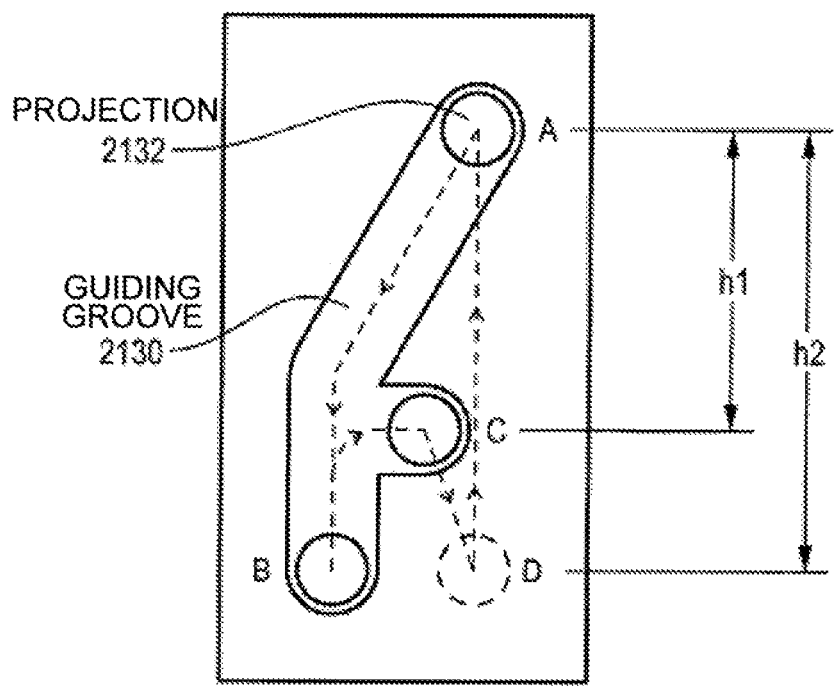
FIG. 5D is a schematic drawing illustrating a second modification of the alternatives of FIGS. 5A and 5B.

FIGS. 5C-5D are schematic drawings illustrating a modification of the alternative of the link motion of FIGS. 5A-5B. In this modification as well, the link motion follows the functioning and structure of the link motion mechanism of a conventional ballpoint pen. The projection 2132 is flexibly connected by means of the flexible bar 2158 (not shown in FIGS. 5C-5D) to the first or second link motion portion, while the guiding groove 2130 is formed in the other one of the first or second link motion portions. When the extraction unit 2000 is pressed a first time, the connection point 2160 of the flexible bar 2158 is moved downwards along a line slightly shifted to the right with respect to a line defined by points A and C. During that movement, the flexible bar 2158 is bent because the projection 2132 is guided within the guiding groove 2130 along a trajectory shown as the dashed line from A to B to C. Due to the detailed structure of the mechanism (not shown here) and provided the downward movement is not too slow, the projection 2132 is biased by the elastic force of the flexible bar 2158 and snaps into the passage to point C only after having reached point B, i.e., in a retracing movement. By pressing the extraction unit 2000 a second time, the projection 2132 (the flexible bar 2158) snaps out of the guiding groove 2130 to allow the extraction unit 2000 to move back along the shifted line. As shown in FIG. 5D, the passage to point C may be shortened compared to that of FIG. 5C. In FIG. 5D, both the movement when the extraction unit 2000 is pressed a first time and the movement when the extraction unit 2000 is pressed a second time are shown by a dashed line having the direction of the arrows.

All of the link motions described herein and illustrated in FIGS. 2A-2B and 5A-5D are applicable to the structures of all delivery systems described with reference to the remaining figures.

Figure 6A:
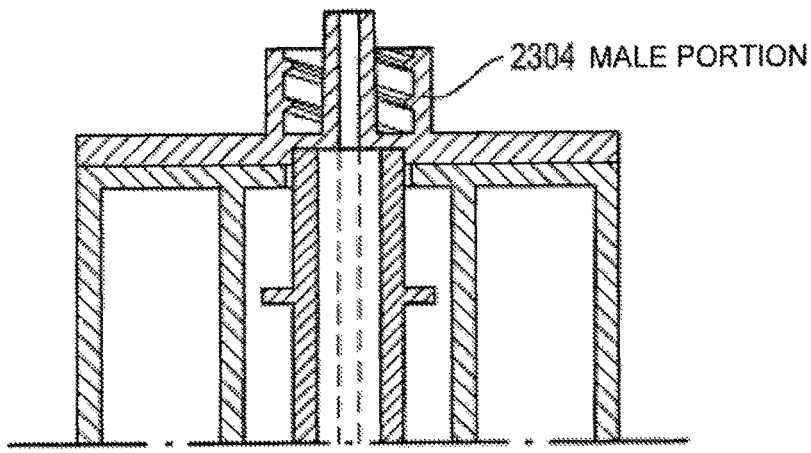
FIG. 6A is a schematic drawing showing another modification of the delivery system according to the present invention.
Figure 6B:
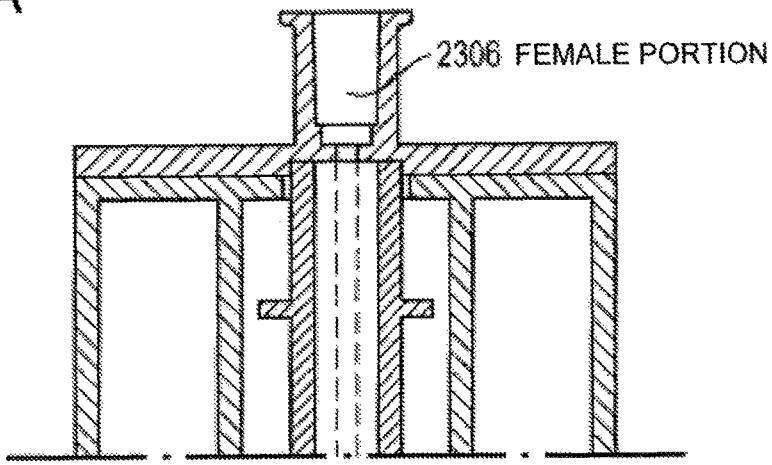
FIG. 6B is a schematic drawing showing yet another modification of the delivery system.
Figure 6C:
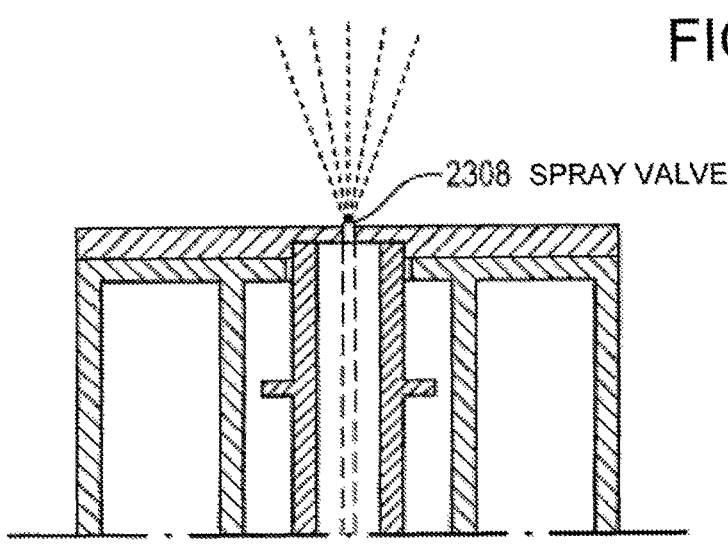
FIG. 6C is a schematic drawing showing yet another modification of the delivery system.

FIGS. 6A-6C show modifications in the type of delivery provided by the delivery system 10. The term "type of delivery" refers to the usage or connectivity of the delivery system 10. Specifically, the hollow needle 2122 may protrude or stick out upwards from the upper end face 2136 of the core portion 2114 (or the first link motion portion 2112) as shown in FIG. 1A in order for the delivery system 10 to be used as syringe. Alternatively, as shown in FIGS. 6A-6B, the delivery system 10 may be coupled by means of a Luer lock connection with a corresponding device, where the rotating element 2300 may be formed to serve as a Luer lock portion, for example, as shown in FIGS. 6A-6B, either as a male portion 2304 as shown in FIG. 6A or as a female portion 2306 as shown in FIG. 6B. The hollow needle 2122 may or may not extend up to the Luer lock portion 2304, 2306. This is indicated in FIGS. 6A-6C by the broken line that may indicate either just the through hole through the core portion 2114 or a portion of the hollow needle 2122.

FIG. 6C illustrates that the delivery system 10 may alternatively be used as a spraying device having a spray valve 2308 instead of a Luer lock connection. Pursuant to the modular design of the delivery system 10, depending on the usage, differently shaped extraction units 2000 or first link motion portions 2112 may be connected to the container unit 2000. As for the hollow needle 2122, the same holds as described with respect to FIGS. 6A-6B.

The operation of the delivery system 10 is described below. The delivery system 10 is shown in its initial state in FIG. 1A. In the initial state, the extraction unit 2000 is coupled to the container 1100 by means of the attachment element 1114, which is part of the container unit 1000. The container 1100 has not yet been actuated in the initial state. In order to penetrate the diaphragm 2140 and the closure element 1200, the hollow needle supporting means 2110 is rotated by means of the rotating element 2300 in order longitudinally to move the hollow needle supporting means 2110 and to press the hollow needle 2122 downward against the force of the compression spring 2120 until the lower end face of the core portion 2114 abuts onto the diaphragm 2140, and the lower tip of the hollow needle 2122 has penetrated the closure element 1200 and is located within the smaller blind hole 1208. This movement is guided by the motion link formed between the guiding groove 2130 of the core portion 2114 and the projection 2132 of the second link motion portion 2118.

FIG. 1B shows the intermediate state, which is achieved when the lower tip of the hollow needle 2122 has penetrated the closure element 1200 and is located within the smaller blind hole 1208. Subsequently, the protecting cap 2310 (and optionally the rotating element 2300) is removed to expose the cannula portion of the hollow needle 2122. Finally, the mounting element 2200 is moved downward by placing the user's forefinger and middle finger onto the finger flange 2208 while pressing the thumb on the container bottom 1104 so that the side wall of the outer portion passes along and outside the side wall 1102 of the container. The squeezing of the user's fingers and thumb moves the side wall 2152 downward and pushes the closure element 1200 like a piston downward until the closure element contacts the container bottom 1104.

FIG. 1C shows the final state. The final state is reached when the closure element 1200 contacts the container bottom 1104. In the final state, essentially all compounds that have been stored in the container 1100 in the initial state have been delivered. When the outer diameter of the rim portion 1106 due to the attachment element 1114 and/or due to the flange 1140 is larger than the outer diameter of the barrel of the container 1100, as shown in FIGS. 1A-1C, the outer circumference of the rim portion 1106 glides along the inner surface of the mounting element 2200, and the side wall 2204 of the mounting element 2200 is not in contact with the outer surface 1110 of the container 1100 below the rim portion 1106. Otherwise, when the outer diameter of the rim portion 1106 is not larger than the outer diameter of the barrel of the container 1100, the inner surface of the side wall 2004 glides in contact along the outer surface 1110 of the container 1100.

Figure 7:
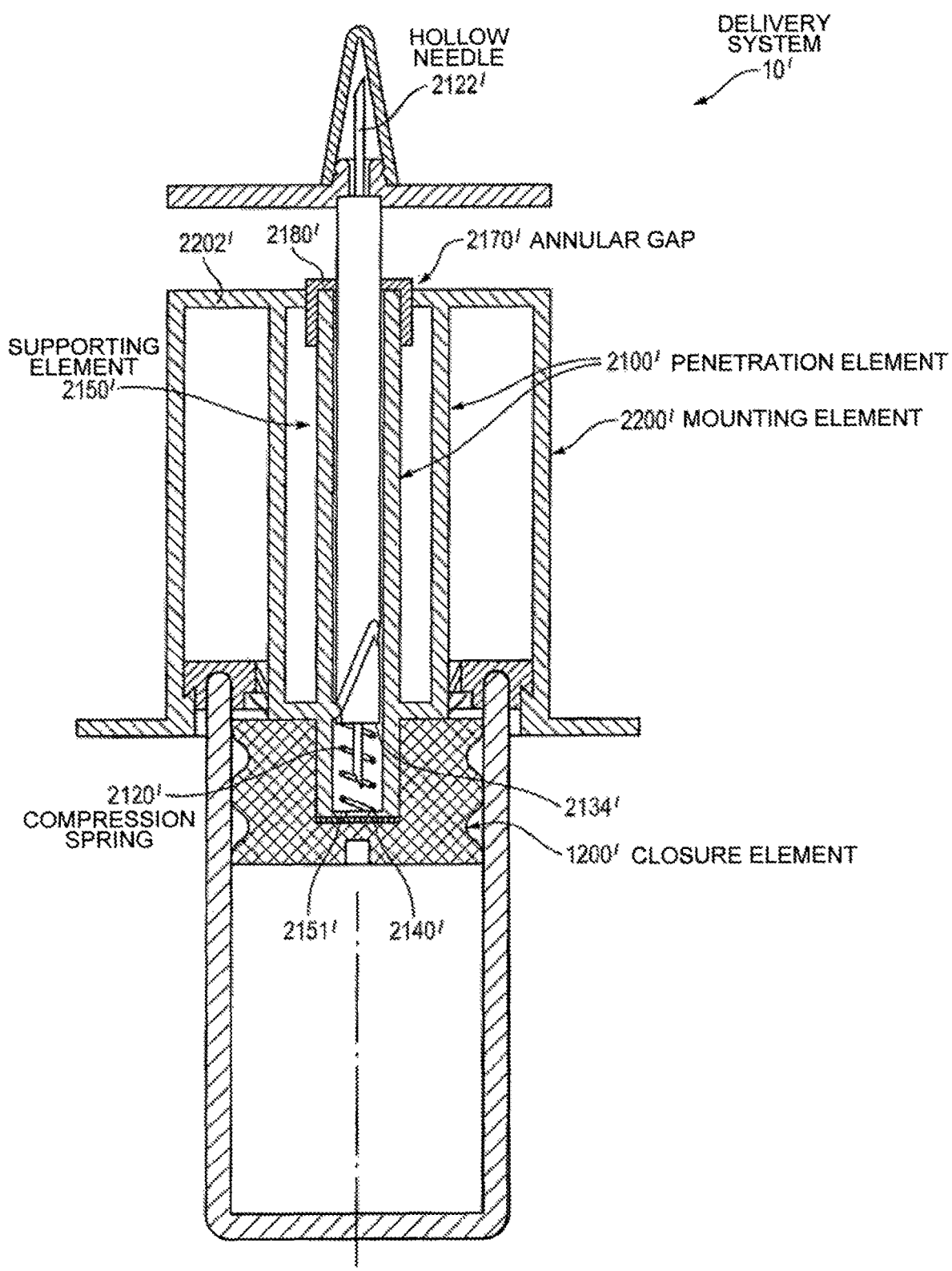
FIG. 7 is a schematic drawing showing a modification of the delivery system of the preferred embodiment shown in FIG. 1A.

FIG. 7 schematically shows yet another embodiment of the delivery system 10. The embodiment of FIG. 7 corresponds in terms of function to the preferred embodiment described above, so no further description on function is provided. In terms of structure, the embodiment of FIG. 7 differs from the preferred embodiment described above only as described below. Similar to the preferred embodiment, the delivery system of FIG. 7 has a compression spring 2120' disposed between the penetration element 2100' and the supporting element 2150'. However, as shown in FIG. 7, the supporting element 2150' forms at its lower end a stopper 2151' for the compression spring 2120'. The compression spring 2120' is an elastic element disposed between the stopper 2151' of the supporting element 2150' and a lower end surface 2134' of the penetration element 2100' that faces the closure element 1200'. The compression spring 2120' surrounds and accommodates the hollow needle 2122' projecting from the lower end surface 2134' of the penetration element 2100'. Furthermore, the supporting element 2150' indirectly abuts the closure element 1200 through the diaphragm 2140' with its lower end that fits into the stopper 2151'.

Unlike the preferred embodiment, the embodiment of FIG. 7 has a supporting element 2150' that extends in a direction opposite the needle penetration direction, i.e., upwards in FIG. 7, until the mounting element bottom 2202'. The penetration element 2100' is disposed within the supporting element 2150' so as to be freely movable in a longitudinal direction. The mounting element bottom 2202' is separated from the upper end of the supporting element 2150' by an annular gap 2170' disposed between the mounting element 2200' and the supporting element 2150'. The annular gap 2170' is closed by a cap-shaped sterility barrier 2180' surrounding the penetration element 2100'. The cap-shaped sterility barrier 2180' is formed of an elastic material, such as a rubber polymer, and sterilely closes the annular gap 2170' by being compressed between the mounting element 2200' and the supporting element 2150'. Furthermore, the cap-shaped sterility barrier 2180' sterilely closes a radial gap between the penetration element 2100' and the supporting element 2150'. In the embodiment of FIG. 7, the compression spring 2120' is disposed between the lower end surface 2134' of the penetration element 2100' and the stopper 2151' of the supporting element 2150'. In yet another embodiment, the compression spring 2120' may be located between the lower end surface 2134' of the penetration element 2100' and the closure element 1200'. In other words, the compression spring 2120' may directly abut the closure element 1200'. Of course, in that case there is no need for the supporting element 2150' to have the stopper 2151'.

REFERENCE NUMERALS 10 delivery system
1000 container unit
1100 container
1102 side wall
1104 container bottom
1106 rim portion
1108 inner surface
1110 outer surface
1112 recession
1114 attachment element
1118 through hole
1120 inner portion
1122 outer portion
1124 circular groove
1126 lower surface
1128 outer end face
1130 inner end face
1132 roof surface
1134 circular detent
1136 lower portion
1138 upper portion
1140 flange 1142 rim portion
1144 circular groove
1200 closure element
1202 outer surface
1204 circular ribs
1206 larger blind hole
1208 smaller blind hole
1210 thin wall portion
1212 upper surface
2000 extraction unit
2100 penetration element 2110 hollow needle supporting means
2112 first link motion portion
2114 core portion
2116 bush portion
2118 second link motion portion
2120 compression spring
2122 hollow needle
2124 upper end face
2126 lower end face
2128 flange
2130 guiding groove
2132 projection
2134 lower end face
2136 upper end face
2138 needle space
2140 diaphragm
2142 end face
2144 lamellas
2150 supporting element
2152 side wall
2154 supporting member bottom
2156 central through hole 2158 flexible bar
2160 connecting point
2200 mounting element
2202 mounting element bottom
2204 side wall
2206 rim portion
2208 finger flange
2210 circular detent
2300 rotating element
2301 central hole
2302 protective cap
2304 male portion of Luer lock
2306 female portion of Luer lock
2308 spray valve
2310 protecting cap
A longitudinal axis
1200' closure element
2100' penetration element
2120' compression spring
2122' hollow needle
2134' lower end surface
2140' diaphragm
2150' supporting element
2151' stopper
2170' annular gap
2180' sterility barrier
2200' mounting element
2202' mounting element bottom Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A delivery system for delivering medical and pharmaceutical compounds, comprising:
    a container adapted to contain the medical and pharmaceutical compounds, wherein the container has a circumferential wall, a first end closed by a container bottom and a second end that is open, and wherein the container unit has a longitudinal axis;
    a closure element disposed within the container in fluid-tight contact with the circumferential wall;
    a supporting element attached to the closure element, wherein the supporting element has a form that locks to the closure element; and
    a penetration element that includes a needle and a first link motion portion, wherein the supporting element includes a second link motion portion, wherein a projection is disposed on one of the first link motion portion or the second link motion portion, wherein the other of the first link motion portion or the second link motion portion has a guiding groove, wherein the needle of the penetration element is adapted to move downwards towards the container bottom and to penetrate the closure element, wherein the penetration element is adapted to move relative to the supporting element along the longitudinal axis towards the container bottom while the projection travels continuously in one rotational direction around the longitudinal axis in the guiding groove, and wherein the guiding groove has a bend such that the projection is adapted to travel in the guiding groove to cause the needle to be moved downwards by a maximum distance when the projection is at the bend and then to continue moving upwards.

2. The delivery system of claim 1, wherein the penetration element is disposed within and longitudinally guided by the supporting element.

3. The delivery system of claim 1, wherein the first link motion portion is adapted to fit into the second link motion portion.

4. The delivery system of claim 1, wherein the container has a rim portion at the second end, wherein an attachment element is fitted onto the container over the rim portion, and wherein the attachment element surrounds and slides along the supporting element.

5. The delivery system of claim 1, wherein the supporting element longitudinally is adapted to guide the penetration element into the closure element.

6. The delivery system of claim 1, further comprising:
    a mounting element connected to the supporting element, wherein the mounting element engages a rim portion of the container at the second end of the container.

7. The delivery system of claim 6, wherein the mounting element includes a finger flange.

8. The delivery system of claim 6, wherein the mounting element is adapted to longitudinally center the penetration element relative to the container.

9. The delivery system of claim 6, wherein an attachment element is disposed on the rim portion, and wherein the mounting element is deformable and adapted to snap over the attachment element to allow the attachment element to slide inside the mounting element.

10. The delivery system of claim 1, wherein the penetration element has a delivery end opposite the closure element, and wherein a spray valve is disposed at the delivery end.

11. The delivery system of claim 1, wherein the penetration element has a delivery end opposite the closure element, and wherein the delivery end is formed as a cannula.

12. The delivery system of claim 1, wherein the closure element has a bottom surface with a first shape, wherein the container bottom has a second shape, and wherein the first shape and the second shape are complementary.

13. The delivery system of claim 1, wherein the closure element has a bottom surface with a blind hole.

14. The delivery system of claim 1, further comprising:
    a compression spring disposed between the penetration element and the closure element.

15. A device, comprising:
a container adapted to contain a liquid, wherein the container has a cylindrical wall, a first end closed by a container bottom and a second end that is open, and wherein the container unit has a central longitudinal axis;
a closure element disposed inside the container that makes fluid-tight contact with the cylindrical wall;
a supporting element attached to the closure element, wherein the supporting element has a form that locks to the closure element; and
a penetration element that has a hollow needle, wherein a projection is disposed on the supporting element, wherein the penetration element has a guiding groove with a bend, wherein the hollow needle of the penetration element is adapted to move a maximum distance towards the container bottom and to penetrate the closure element, wherein the penetration element is adapted to move relative to the supporting element along the longitudinal axis towards the container bottom while the projection travels continuously in one rotational direction around the longitudinal axis in the guiding groove, wherein the guiding groove is shaped so as to cause the hollow needle to be moved the maximum distance downwards to penetrate the closure element when the projection is at the bend, and wherein the guiding groove is shaped so as to cause the projection to continue moving upwards past the bend in the guiding groove so as to cause the hollow needle to retract.

16. The device of claim 15, wherein the supporting element is adapted to longitudinally guide the penetration element into the closure element.

17. The device of claim 15, further comprising:
a mounting element connected to the supporting element, wherein the mounting element includes a finger flange, and wherein the mounting element engages the container at the second end of the container.

18. The device of claim 15, wherein the penetration element has a cannula opposite the hollow needle.

19. The device of claim 15, wherein the closure element has a bottom surface with a blind hole.

20. The device of claim 15, further comprising:
a compression spring disposed between the penetration element and the closure element.

21. A delivery system for delivering medical and pharmaceutical compounds, comprising:
a container adapted to contain the medical and pharmaceutical compounds, wherein the container has a circumferential wall, a first end closed by a container bottom, a second end that is open and a rim portion at the second end, and wherein the container unit has a longitudinal axis;
a closure element disposed within the container in fluid-tight contact with the circumferential wall;
a supporting element attached to the closure element, wherein the supporting element has a form that locks to the closure element;
a mounting element connected to the supporting element, wherein the mounting element includes a finger flange, and wherein the rim portion is adapted to slide inside the mounting element; and
a penetration element that includes a needle and a first link motion portion, wherein the supporting element includes a second link motion portion, wherein a projection is disposed on one of the first link motion portion or the second link motion portion, wherein the other of the first link motion portion or the second link motion portion has a guiding groove, wherein the needle of the penetration element is adapted to move a maximum distance towards the container bottom in order to penetrate the closure element, wherein the penetration element is adapted to move relative to the supporting element along the longitudinal axis towards the container bottom while the projection travels continuously in one rotational direction around the longitudinal axis in the guiding groove; and wherein the guiding groove has a bend such that the projection is adapted to travel in the guiding groove to cause the needle to be moved downwards by the maximum distance when the projection is at the bend and then to continue moving upwards.

22. The delivery system of claim 1, wherein the form of the supporting element is adapted to lock to the closure element by screwing into the closure element.

* * * * *